United States Patent
Kordes et al.

(10) Patent No.: US 7,655,600 B2
(45) Date of Patent: Feb. 2, 2010

(54) 1-(AZOLIN-2-YL)AMINO-1,2-DIPHENYLETHANE COMPOUNDS FOR COMBATING INSECTS, ARACHNIDS AND NEMATODES

(75) Inventors: Markus Kordes, Frankenthal (DE); Michael Hofmann, Ludwigshafen (DE); Michael Puhl, Lampertheim (DE); Norbert Götz, Worms (DE); Michael Rack, Heidelberg (DE); Ernst Baumann, Dudenhofen (DE); Wolfgang von Deyn, Neustadt (DE); Thomas Schmidt, Neustadt (DE); Livio Tedeschi, Mannheim (DE); Michael F. Treacy, Corpus Christi, TX (US); Deborah L. Culbertson, Fuquay Varina, NC (US); Toni Bucci, Fuquay Varina, NC (US); David G. Kuhn, Apex, NC (US)

(73) Assignee: BASF Aktiengesellschaft, Ludwigshafen (DE)

( * ) Notice: Subject to any disclaimer, the term of this patent is extended or adjusted under 35 U.S.C. 154(b) by 468 days.

(21) Appl. No.: 10/583,710

(22) PCT Filed: Dec. 22, 2004

(86) PCT No.: PCT/EP2004/014623

§ 371 (c)(1),
(2), (4) Date: Jun. 20, 2006

(87) PCT Pub. No.: WO2005/063724

PCT Pub. Date: Jul. 14, 2005

(65) Prior Publication Data

US 2007/0149582 A1    Jun. 28, 2007

Related U.S. Application Data

(60) Provisional application No. 60/531,612, filed on Dec. 23, 2003.

(51) Int. Cl.
*A01N 43/76* (2006.01)
*A01N 43/78* (2006.01)
*C07D 277/04* (2006.01)
*C07D 277/08* (2006.01)

(52) U.S. Cl. ............ 504/266; 548/146; 548/190; 548/215; 548/233; 504/261

(58) Field of Classification Search ............ 548/146, 548/190, 215, 233; 504/261, 266
See application file for complete search history.

(56) References Cited

OTHER PUBLICATIONS

Kaye et al (1952): STN International HCAPLUS database, (Columbus, Ohio), Accession No. 1954:826.*
Hirashima, A., et al. "Synthesis and Octopaminergic Agonist Activity of 2-(Substituted benzylamino)-2-thiazolines", Biosci. Biotech. Biochem., 1992, pp. 1061-1065, vol. 56, No. 7, Search Report.
Jennings, K.R., et al., "A Biorationally Synthesized Octopaminergic Insecticide 2-(4-Chloro-o-toluidino)-2-oxazoline", Pesticide Biochemistry and Physiology, 1988, pp. 190-197, vol. 30, Search Report.

* cited by examiner

*Primary Examiner*—Golam M Shameem
(74) *Attorney, Agent, or Firm*—Brinks Hofer Gilson & Lione

(57) ABSTRACT

The present invention relates to 1-(azolin-2-yl)amino-1,2-diphenylethane compounds of the general formula (I) wherein A is a radical of the formulae A¹ or A²: NRA'A² and wherein m is 0, 1, 2, 3, 4 or 5, n is 0, 1, 2, 3, 4 or 5, X is sulfur or oxygen, and wherein the variables $R^1$, $R^2$, $R^3$, $R^4$, $R^{5a}$, $R^{5b}$, $R^{5c}$, $R^{5d}$ are as defined in the claims, and to the agriculturally acceptable salts thereof. The invention relates also to a method of combating animal pests, selected from insects, arachnids and nematodes and to a method for protecting crops from attack or infestation by insects, arachnids or nematodes, which comprises contacting a crop with a pesticidally effective amount of a 1-(azolin-2-yl)amino-1,2-diphenylethane compounds of the general formula I and/or at least one salt thereof.

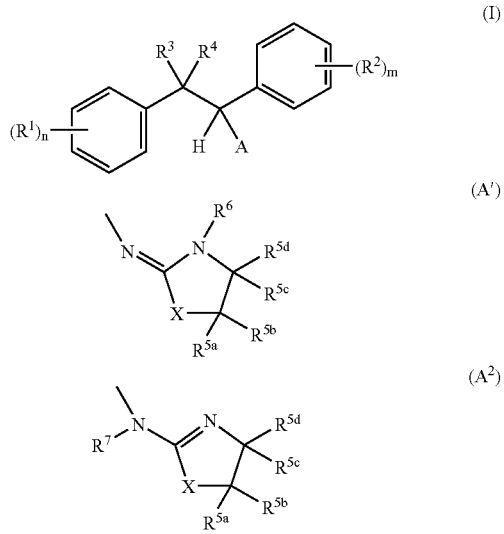

18 Claims, No Drawings

1-(AZOLIN-2-YL)AMINO-1,2-DIPHENYLETHANE COMPOUNDS FOR COMBATING INSECTS, ARACHNIDS AND NEMATODES

This application is a National Stage application of International Application No. PCT/EP2004/014623, filed Dec. 22, 2004, which claims the benefit of U.S. Provisional Application No. 60/531,612, filed Dec. 23, 2003, the entire contents of which are hereby incorporated herein by reference in its entirety.

The present invention relates to 1-(azolin-2-yl)amino-1,2-diphenylethane compounds which are useful for combating insects, arachnids and nematodes. The present invention also relates to a method for combating animal pests selected from insects, arachnids and nematodes, and to agricultural compositions for combating animal pests.

Animal pests and in particular insects, arachnids and nematodes destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating insects, arachnids and nematodes.

Jennings et al. Pesticide Biochemistry and Physiology 30, 1988, p. 190-197 describe several 2-phenylamino oxazolines and 2-benzylamino oxazolines which have insecticidal activity. Biosci. Biotech. Biochem. 1992, 56 (7), 1062-1065 discloses phenyl-, benzyl-und phenethyl thiazolines having insecticidal activity. However, these compounds are limited in their activity or with regard to breadth of their activity spectrum.

It is therefore an object of the present invention to provide compounds having a good pesticidal activity and show a broad activity spectrum against a large number of different animal pests, especially against difficult to control insects, arachnids and nematodes.

It has been found that these objectives can be achieved by 1-(azolin-2-yl)amino-1,2-diphenylethane compounds of the general formula I:

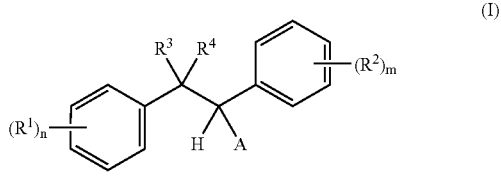

(I)

wherein A is a radical of the formulae $A^1$ or $A^2$:

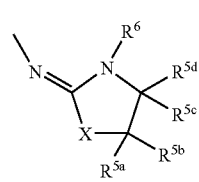

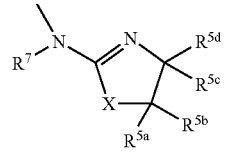

and wherein
m is 0, 1, 2, 3, 4 or 5;
n is 0, 1, 2, 3, 4 or 5;
X is sulfur or oxygen;
$R^1$, $R^2$ are each independently halogen, OH, SH, $NH_2$, $SO_3H$, COOH, cyano, nitro, $C_1$-$C_6$-alkyl, $C_1$-$C_6$-alkoxy, $C_1$-$C_6$-alkylamino, di($C_1$-$C_6$-alkyl)amino, $C_1$-$C_8$-alkylthio, $C_2$-$C_6$-alkenyl, $C_2$-$C_6$-alkenyloxy, $C_2$-$C_6$-alkenylamino, $C_2$-$C_6$-alkenylthio, $C_2$-$C_6$-alkynyl, $C_2$-$C_6$-alkynyloxy, $C_2$-$C_6$-alkynylamino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkynylsulfonyl, formyl, $C_1$-$C_6$-alkylcarbonyl, $C_2$-$C_6$-alkenylcarbonyl, $C_2$-$C_6$-alkynylcarbonyl, $C_1$-$C_6$-alkoxycarbonyl, $C_2$-$C_6$-alkenyloxycarbonyl, $C_2$-$C_6$-alkynyloxycarbonyl, carbonyloxy (=HC(O)— or formyloxy), $C_1$-$C_6$-alkylcarbonyloxy, $C_1$-$C_6$-alkenylcarbonyloxy, $C_1$-$C_6$-alkynylcarbonyloxy, wherein the carbon atoms in the aliphatic radicals of the aforementioned groups may carry any combination of 1, 2 or 3 radicals $R^\#$,
$C(O)NR^aR^b$, $(SO_2)NR^aR^b$, wherein $R^a$ and $R^b$ are each independently hydrogen, $C_1$-$C_6$-alkyl, $C_2$-$C_6$-alkenyl, or $C_2$-$C_6$-alkynyl, wherein the carbon atoms in these groups may carry any combination of 1, 2 or 3 radicals $R^\#$,
a radical Y—Ar or a radical Y—Cy, wherein
Y is a single bond, oxygen, sulfur, $C_1$-$C_6$-alkandiyl or $C_1$-$C_6$-alkandiyloxy,
Ar is phenyl, naphthyl or a mono- or bicyclic 5- to 10-membered heteroaromatic ring, which contains 1,2, 3 or 4 heteroatoms selected from oxygen, sulfur and nitrogen as ring members, wherein Ar is unsubstituted or may carry any combination of 1, 2, 3, 4 or 5 radicals $R^\#$; and
Cy is $C_3$-$C_{12}$-cycloalkyl, which is unsubstituted or substituted with any combination of 1, 2, 3, 4 or 5 radicals $R^\#$;
and wherein two radicals $R^1$ or two radicals $R^2$ that are bound to adjacent carbon atoms of the phenyl rings may form together with said carbon atoms a fused benzene ring, a fused saturated or partially unsaturated 5-, 6-, or 7-membered carbocycle or a fused 5-, 6-, or 7-membered heterocycle, which contains 1, 2, 3 or 4 heteroatoms selected from oxygen, sulfur and nitrogen as ring members, and wherein the fused ring is unsubstituted or may carry any combination of 1, 2, 3, or 4 radicals $R^\#$;
$R^3$, $R^4$ are each independently hydrogen, $C_1$-$C_6$-alkyl, $C_1$-$C_6$-haloalkyl, $C_3$-$C_6$-cycloalkyl, wherein the carbon atoms in these groups may carry any combination of 1, 2 or 3 radicals $R^\#$,
phenyl or benzyl, each unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups;
$R^{5a}$, $R^{5b}$, $R^{5c}$, $R^{5d}$ are each independently hydrogen, $C_1$-$C_6$-alkyl, $C_1$-$C_6$-haloalkyl, $C_1$-$C_6$-alkylamino, $C_1$-$C_6$-alkoxy, $C_3$-$C_6$-cycloalkyl, wherein the carbon atoms in these groups may carry any combination of 1, 2 or 3 radicals $R^\#$, halogen, cyano, nitro, hydroxy, mercapto, amino, phenyl or benzyl, each unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups;

$R^6$ is hydrogen, cyano, nitro, $C_1$-$C_6$-alkyl, formyl, $C_1$-$C_6$-alkylcarbonyl, $C_1$-$C_6$-alkoxycarbonyl, $C_1$-$C_6$-alkylthiocarbonyl, wherein the carbon atoms in the aliphatic radicals of the aforementioned groups may carry any combination of 1, 2 or 3 radicals $R^\#$, $C(O)NR^aR^b$, or $(SO_2)NR^aR^b$, wherein $R^a$ and $R^b$ are as defined above, phenyl, phenyloxy, or benzyl, each of the last three mentioned radicals may be unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups;

$R^7$ is hydrogen, cyano, nitro, $C_1$-$C_6$-alkyl, formyl, $C_1$-$C_6$-alkylcarbonyl, $C_1$-$C_6$-alkoxycarbonyl, $C_1$-$C_6$-alkylthiocarbonyl, wherein the carbon atoms in the aliphatic radicals of the aforementioned groups may carry any combination of 1, 2 or 3 radicals $R^\#$, $C(O)NR^aR^b$, or $(SO_2)NR^aR^b$, wherein $R^a$ and $R^b$ are as defined above, phenyl, phenyloxy or benzyl, each of the last three mentioned groups may be unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups; and $R^\#$ is halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy, or $C_1$-$C_6$-alkylthio;

and by the agriculturally acceptable salts of compounds of the formula I.

Therefore, the present invention relates to 1-(azolin-2-yl)amino-1,2-diphenylethane compounds of the general formula I and to the agriculturally acceptable salts thereof. These compounds have a high pesticidal activity and are active against a broad spectrum of animal pests selected from insects, arachnids and nematodes.

Therefore the invention relates also to a method of combating animal pests, selected from insects, arachnids and nematodes, which comprises contacting the animal pests, their habit, breeding ground, food supply, plant, seed, soil, area, material or environment in which the animal pests are growing or may grow, or the materials, plants, seeds, soils, surfaces or spaces to be protected from I attack or infestation by insects, arachnids or nematodes with a pesticidally effective amount of at least one 1-(azolin-2-yl)amino-1,2-diphenylethane compounds of the general formula I of the general formula I and/or at least one agriculturally acceptable salt thereof.

Furthermore, the present invention provides a method for protecting crops from attack or infestation by insects, arachnids or nematodes, which comprises contacting a crop with a pesticidally effective amount of a 1-(azolin-2-yl)amino-1,2-diphenylethane compounds of the general formula I and/or at least one salt thereof.

Furthermore, the invention relates to agricultural compositions, preferably in the form of directly sprayable solutions, emulsions, pastes oil dispersions, powders, materials for scattering, dusts or in the form of granules, which comprise at least one 1-(azolin-2-yl)amino-1,2-diphenylethane compound of the general formula I as defined above or a salt thereof, admixed with one or more agronomically acceptable inert, solid or liquid carrier(s) and, if desired, at least one surfactant.

The compounds of the general formula I may have one or more centers of chirality, in which case they are present as mixtures of enantiomers or diastereomers. The present invention provides both the pure enantiomes or diastereomers or mixtures thereof. The compounds of the general formula I may also exist in the form of different tautomers. The invention comprises the single tautomers, if separable, as well as the tautomer mixtures.

Salts of the compounds of the formula I are especially agriculturally acceptable salts. They can be formed in a customary method, e.g. by reacting the compound with an acid of the anion in question if the compound of formula I has a basic functionality or by reacting an acidic compound of formula I with a suitable base.

Suitable agriculturally useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae Ia and Ib with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

Examples of other meanings are:

The term "$C_1$-$C_6$-alkyl" as used herein and in the alkyl moieties of $C_1$-$C_6$-alkoxy, $C_1$-$C_6$-alkylamino, di($C_1$-$C_6$-alkyl)amino, $C_1$-$C_6$-alkylthio, $C_1$-$C_6$-alkylsulfonyl, $C_1$-$C_6$-alkylsulfoxyl, $C_1$-$C_6$-alkylcarbonyl, $C_1$-$C_6$-alkoxycarbonyl, $C_1$-$C_6$-alkylthiocarbonyl, and $C_1$-$C_6$-alkylcarbonyloxy refer to a saturated straight-chain or branched hydrocarbon group having 1 to 6 carbon atoms, especially 1 to 4 carbon groups, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

In each alkyl radical the carbon atoms may carry 1, 2 or 3 radicals $R^\#$. In other words, each of the hydrogen atoms in these radicals may independently from the others be replaced by one of the aforementioned radicals $R^\#$. In case of $R^\#$ being halogen usually 1, 2, 3 or all of the hydrogen atoms in said alkyl radical are replaced by halogen, especially by fluorine or chlorine. These radicals are also referred to as haloalkyl. In case of $R^\#$ being cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy, or $C_1$-$C_6$-alkylthio usually 1 or 2 of the hydrogen atoms in said alkyl radikal may be replaced by the radical $R^\#$.

The term "$C_1$-$C_6$-haloalkyl" as used herein refers to a straight-chain or branched saturated alkyl group having 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term, "$C_1$-$C_6$-alkoxy" as used herein refers to a straight-chain or branched saturated alkyl group having 1 to 6 carbon atoms (as mentioned above) which is attached via an oxygen atom. Examples include $C_1$-$C_6$-alkoxy such as methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "$C_1$-$C_6$-haloalkoxy" as used herein refers to a $C_1$-$C_6$-alkoxy group as mentioned above wherein the hydrogen atoms are partially or fully substituted by fluorine, chlorine, bromine and/or iodine, i.e., for example, $C_1$-$C_6$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy.

The term "$C_1$-$C_6$-alkoxy-$C_1$-$C_6$-alkyl" as used herein refers to $C_1$-$C_6$-alkyl wherein 1 carbon atom carries a $C_1$-$C_6$-alkoxy radical as mentioned above. Examples are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl and the like.

The term "$C_1$-$C_6$-alkylcarbonyl" as used herein refers to a straight-chain or branched saturated alkyl group having 1 to 6 carbon atoms (as mentioned above) bonded via the carbon atom of the carbonyl group at any bond in the alkyl group. Examples include $C_1$-$C_6$-alkylcarbonyl such CO—$CH_3$, CO—$C_2H_5$, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl and the like.

The term "$C_1$-$C_6$-alkoxycarbonyl" as used herein refers to a straight-chain or branched alkoxy group (as mentioned above) having 1 to 6 carbon atoms attached via the carbon atom of the carbonyl group. Examples include ($C_1$-$C_6$-alkoxy)carbonyl, for example CO—$OCH_3$, CO—$OC_2H_5$, COO—$CH_2$—$C_2H_5$, CO—$OCH(CH_3)_2$, n-butoxycarbonyl, CO—$OCH(CH_3)$—$C_2H_5$, CO—$OCH_2$—$CH(CH_3)_2$, CO—$OC(CH_3)_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl The term "$C_1$-$C_6$-alkylcarbonyloxy" as used herein refers to a straight-chain or branched saturated alkyl group having 1 to 6 carbon atoms (as mentioned above) bonded via the carbon atom of the carbonyloxy group at any bond in the alkyl group. Examples include $C_1$-$C_6$-alkylcarbonyloxy such O—CO—$CH_3$, O—CO—$C_2H_5$, n-propylcarbonyloxy, 1-methylethylcarbonyloxy, n-butylcarbonyloxy, 1-methylpropylcarbonyloxy, 2-methylpropylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropylcarbonyloxy, 1,2-dimethylpropylcarbonyloxy and the like.

The term "$C_1$-$C_6$-alkylthio ($C_1$-$C_6$-alkylsulfanyl: $C_1$-$C_6$-alkyl-S—)" as used herein refers to a straight-chain or branched saturated alkyl group having 1 to 6 carbon atoms (as mentioned above) which is attached via a sulfur atom, for example $C_1$-$C_4$-alkylthio such as methylthio, ethylthio, propylthio, 1-methylethylthio, butylthio, 1-methylpropylthio, 2-methylpropylthio, 1,1-dimethylethylthio, n-pentylthiocarbonyl, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutythio, 2,2-dimethylbutylthio, 2,3-dimethylbutylthio, 3,3-dimethylbutylthio, 1-ethylbutlthio, 2-ethylbutylthio, 1,1,2-trimethylpropylthio, 1,2,2-trimethylpropylthio, 1-ethyl-1-methylpropylthio or 1-ethyl-2-methylpropylthio.

The term "$C_1$-$C_6$-alkylthiocarbonyl" as used herein refers to a straight-chain or branched alkthio group (as mentioned above) having 1 to 6 carbon atoms attached via the carbon atom of the carbonyl group. Examples include CO—$SCH_3$, CO—$SC_2H_5$, CO—$SCH_2$—$C_2H_5$, CO—$SCH(CH_3)_2$, n-butylthiocarbonyl, CO—$SCH(CH_3)$—$C_2H_5$, CO—$SCH_2$—CH$(CH_3)_2$, CO—$SC(CH_3)_3$, n-pentylthiocarbonyl, 1-methylbutylthiocarbonyl, 2-methylbutylthiocarbonyl, 3-methylbutylthiocarbonyl, 2,2-dimethylpropylthiocarbonyl, 1-ethylpropylthiocarbonyl, n-hexylthiocarbonyl, 1,1-dimethylpropylthiocarbonyl, 1,2-dimethylpropylthiocarbonyl, 1-methylpentylthiocarbonyl, 2-methylpentylthiocarbonyl, 3-methylpentylthiocarbonyl, 4-methylpentylthiocarbonyl, 1,1-dimethylbutylthiocarbonyl, 1,2-dimethylbutylthiocarbonyl, 1,3-dimethylbutythiocarbonyl, 2,2-dimethylbutylthiocarbonyl, 2,3-dimethylbutylthiocarbonyl, 3,3-dimethylbutylthiocarbonyl, 1-ethylbutlthioycarbonyl, 2-ethylbutylthiocarbonyl, 1,1,2-trimethylpropylthiocarbonyl, 1,2,2-trimethylpropylthiocarbonyl, 1-ethyl-1-methylpropylthiocarbonyl or 1-ethyl-2-methylpropylthiocarbonyl The term "$C_1$-$C_6$-alkylsulfinyl" ($C_1$-$C_6$-alkylsulfoxyl: $C_1$-$C_6$-alkyl-S(=O)—), as used herein refers to a straight-chain or branched saturated hydrocarbon group (as mentioned above) having 1 to 6 carbon atoms bonded through the sulfur atom of the sulfinyl group at any bond in the alkyl group. Examples include $C_1$-$C_6$-alkylsulfinyl: SO—$CH_3$, SO—$C_2H_5$, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The term "$C_1$-$C_6$-alkylamino" refers to a secondary amino group carrying one alkyl group as defined above e.g. methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino, 1-ethyl-2-methylpropylamino.

The term "di($C_1$-$C_6$-alkyl)amino" refers to a tertiary amino group carrying two alkyl radicals as defined above e.g. dimethylamino, diethylamino, di-n-propylamino, diisopropylamino, N-ethyl-N-methylamino, N-(n-propyl)-N-methylamino, N-(isopropyl)-N-methylamino, N-(n-butyl)-N-methylamino, N-(n-pentyl)-N-methylamino, N-(2-butyl)-N-methylamino, N-(isobutyl)-N-methylamino, N-(n-pentyl)-N-methylamino, N-(n-propyl)-N-ethylamino, N-(isopropyl)-N-ethylamino, N-(n-butyl)-N-ethylamino, N-(n-pentyl)-N-ethylamino, N-(2-butyl)-N-ethylamino, N-(isobutyl)-N-ethylamino, N-(n-pentyl)-N-ethylamino, etc.

The term "$C_1$-$C_6$-alkylsulfonyl" ($C_1$-$C_6$-alkyl-S(=O)$_2$—) as used herein refers to a straight-chain or branched saturated alkyl group having 1 to 6 carbon atoms (as mentioned above) which is bonded via the sulfur atom of the sulfonyl group at any bond in the alkyl group. Examples include $C_1$-$C_6$-alkylsulfonyl such as $SO_2$—$CH_3$, $SO_2$—$C_2H_5$, n-propylsulfonyl, $SO_2$—$CH(CH_3)_2$, n-butylsulfonyl, 1-methylpropylsulfonyl, 2-methylpropylsulfonyl, $SO_2$—$C(CH_3)_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl and the like.

The term "$C_2$-$C_6$-alkenyl" as used herein and in the alkenyl moieties of $C_2$-$C_6$-alkenyloxy, $C_2$-$C_6$-alkenylamino, $C_2$-$C_6$-alkenylthio, $C_2$-$C_6$-alkenylsulfonyl, $C_2$-$C_6$-alkenylcarbonyl, $C_2$-$C_6$-alkenyloxycarbonyl, and $C_2$-$C_6$-alkenylcarbonyloxy refers to a straight-chain or branched unsaturated hydrocarbon group having 2 to 6 carbon atoms and a double bond in any position, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2- butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

In each alkenyl radical the carbon atoms may carry 1, 2 or 3 radicals $R^{\#}$. In other words, each of the hydrogen atoms in these radicals may independently from the others be replaced by one of the aforementioned radicals $R^{\#}$. In case of $R^{\#}$ being halogen usually 1, 2, 3 or all of the hydrogen atoms in said alkyl radical are replaced by halogen, especially by fluorine or chlorine. These radicals are also referred to as haloalkyl. In case of $R^{\#}$ being cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy, or $C_1$-$C_6$-alkylthio usually 1 or 2 of the hydrogen atoms in said alkyl radikal may be replaced by the radical $R^{\#}$.

The term, "$C_2$-$C_6$-alkenyloxy" as used herein refers to a straight-chain or branched saturated alkenyl group having 2 to 6 carbon atoms (as mentioned above) which is attached via an oxygen atom, such as vinyloxy, allyloxy (propen-3-yloxy), methallyloxy, buten-4-yloxy, etc.

The term "$C_2$-$C_6$-alkenylthio" as used herein refers to a straight-chain or branched saturated alkenyl group having 2 to 6 carbon atoms (as mentioned above) which is attached via a sulfur atom, for example vinylsulfanyl, allylsulfanyl (propen-3-ylthio), methallylsufanyl, buten-4-ylsulfanyl, etc.

The term "$C_2$-$C_6$-alkenylamino" as used herein refers to a straight-chain or branched saturated alkenyl group having 2 to 6 carbon atoms (as mentioned above) which is attached via a sulfur atom, for example vinylamino, allylamino (propen-3-ylamino), methallylamino, buten-4-ylamino, etc.

The term "$C_2$-$C_6$-alkenylsulfonyl" as used herein refers to a straight-chain or branched saturated alkenyl group having 2 to 6 carbon atoms (as mentioned above) which is attached via a sulfonyl ($SO_2$) group, for example vinylsulfonyl, allylsulfonyl (propen-3-ylsulfonyl), methallylsufonyl, buten-4-ylsulfonyl, etc.

The term "$C_2$-$C_6$-alkynyl" as used herein and in the alkynyl moieties of $C_2$-$C_6$-alkynyloxy, $C_2$-$C_6$-alkynylamino, $C_2$-$C_6$-alkynylthio, $C_2$-$C_6$-alkynylsulfonyl, $C_2$-$C_6$-alkynylcarbonyl, $C_2$-$C_6$-alkynyloxycarbonyl, and $C_1$-$C_6$-alkynylcarbonyloxy refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

In each alkynyl radical the carbon atoms may carry 1, 2 or 3 radicals $R^{\#}$. In other words, each of the hydrogen atoms in these radicals may independently from the others be replaced by one of the aforementioned radicals $R^{\#}$. In case of $R^{\#}$ being halogen usually 1, 2, 3 or all of the hydrogen atoms in said alkyl radical are replaced by halogen, especially by fluorine or chlorine. These radicals are also referred to as haloalkyl. In case of $R^{\#}$ being cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy, or $C_1$-$C_6$-alkylthio usually 1 or 2 of the hydrogen atoms in said alkyl radikal may be replaced by the radical $R^{\#}$.

The term, "$C_2$-$C_6$-alkynyloxy" as used herein refers to a straight-chain or branched saturated alkynyl group having 2 to 6 carbon atoms (as mentioned above) which is attached via an oxygen atom, such as propargyloxy (propin-3-yloxy), butin-3-yloxy, butin-4-yloxy, etc.

The term "$C_2$-$C_6$-alkynylthio" as used herein refers to a straight-chain or branched saturated alkynyl group having 2 to 6 carbon atoms (as mentioned above) which is attached via a sulfur atom, for example propargylsulfanyl (propin-3-ylthio), butin-3-ylsufanyl, butin-4-ylsulfanyl, etc.

The term "$C_2$-$C_6$-alkynylamino" as used herein refers to a straight-chain or branched saturated alkynyl group having 2 to 6 carbon atoms (as mentioned above) which is attached via a sulfur atom, for example propargylamino (propin-3-ylamino), butin-3-amino, butin-4-ylamino, etc.

The term "$C_2$-$C_6$-alkynylsulfonyl" as used herein refers to a straight-chain or branched saturated alkynyl group having 2 to 6 carbon atoms (as mentioned above) which is attached via a sulfonyl ($SO_2$) group, for example propargylsulfonyl (propin-3-yltsulfonyl), butin-3-ylsufonyl, butin-4-ylsulfonyl, etc.

The term "$C_3$-$C_{12}$-cycloalkyl" as used herein refers to a mono- or bi- or polycyclic hydrocarbon radical having 3 to 12 carbon atoms, in particular 3 to 6 carbon atoms. Examples of monocyclic radicals comprise cyclopropyl, cyclobutyl, cyclopentyl, cyclohexyl, cycloheptyl, cyclooctyl, cyclononyl or cyclodecyl. Examples of bicyclic radicals comprise bicyclo[2.2.1]heptyl, bicyclo[3.1.1]heptyl, bicyclo[2.2.2]octyl, and bicyclo[3.2.1]nonyl. Examples of tricylcic radicals are adamantyl and homoadamantyl.

Each cycloalkyl radical may carry 1, 2, 3, 4 or 5 of the aforementioned radicals $R^{\#}$. In other words, 1, 2, 3, 4 or 5 of the hydrogen atoms in these radicals may independently from the others be replaced by one of the aforementioned radicals $R^{\#}$. Preferred radicals $R^{\#}$ on cycloalkyl are selected from halogen, especially fluorine or chlorine, and $C_1$-$C_6$-alkyl.

The term "mono- or biclyic heteroaromatic ring" as used herein refers to a monocyclic heteroaromatic radical which has 5 or 6 ring members, which may comprise a fused 5, 6 or 7 membered ring thus having a total number of ring members from 8 to 10, wherein in each case 1, 2, 3 or 4 of these ring members are heteroatoms selected, independently from each other, from the group consisting of oxygen, nitrogen and sulfur. The heterocyclic radical may be attached to the remainder of the molecule via a carbon ring member or via a nitrogen ring member. The fused ring comprises $C_5$-$C_7$-cycloalkyl, $C_5$-$C_7$-cycloalkenyl, or 5 to 7 membered heterocyclyl and phenyl.

Examples for monocyclic 5- to 6-membered heteroaromatic rings include triazinyl, pyrazinyl, pyrimidyl, pyridazinyl, pyridyl, thienyl, furyl, pyrrolyl, pyrazolyl, imidazolyl, triazolyl, tetrazolyl, thiazolyl, oxazolyl, thiadiazolyl, oxadiazolyl, isothiazolyl and isoxazolyl.

Examples for 5- to 6-membered heteroaromatic rings carrying a fused phenyl ring are quinolinyl, isoquinolinyl, indolyl, indolizinyl, isoindolyl, indazolyl, benzofuryl, benzthienyl, benzo[b]thiazolyl, benzoxazolyl, benzthiazolyl, benzoxazolyl, and benzimidazolyl. Examples for 5- to 6-membered heteroaromatic rings carrying a fused cycloalkenyl ring are dihydroindolyl, dihydroindolizinyl, dihydroisoindolyl, dihydrochinolinyl, dihydroisochinolinyl, chromenyl, chromanyl and the like.

The term "5 to 7 membered heterocyclyl" comprises monocyclic heteroaromatic rings as defined above and nonaromatic saturated or partially unsaturated heterocyclic rings having 5, 6 or 7 ring members. Examples for non-aromatic rings include pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, dioxanyl, thiopyranyl, dihydrothiopyranyl, tetrahydrothiopyranyl, morpholinyl, thiazinyl and the like.

As regards the pesticidal activity of the compounds of general formula I, preference is given to those compounds of the formula I, wherein the variables n, m, $R^1$, $R^2$, $R^3$, $R^4$ $R^{5a}$, $R^{5b}$, $R^{5c}$, $R^{5d}$ $R^6$ and $R^7$ have independently of each other or more preferably in combination the following meanings.

n is 0, 1 or 2;
m is 0, 1 or 2;
m+n=0, 1, 2, 3 or 4, especially 1, 2, 3 or 4;
$R^1$ halogen, $C_1$-$C_4$-alkyl, $C_1$-$C_4$-alkoxy, $C_1$-$C_4$-haloalkyl, and phenyl, which is unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups, especially fluorine, chlorine, bromine, methyl, ethyl, methoxy, ethoxy, difluoromethyl, trifluoromethyl, difluormethoxy, trifluormethoxy, methylthio or phenyl, which may be unsubstituted or may carry 1, 2 or 3 radicals selected from halogen or methyl;
$R^2$ halogen, $C_1$-$C_4$-alkyl, $C_1$-$C_4$-alkoxy, $C_1$-$C_4$-haloalkyl, and phenyl, which is unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups, especially fluorine, chlorine, bromine, methyl, ethyl, methoxy, ethoxy, difluoromethyl, trifluoromethyl, difluormethoxy, trifluormethoxy, methylthio or phenyl, which may be unsubstituted or may carry 1, 2 or 3 radicals selected from halogen or methyl;
$R^3$ hydrogen or $C_1$-$C_4$-alkyl, especially hydrogen or methyl and most preferred hydrogen;
$R^4$ hydrogen, $C_1$-$C_4$-alkyl, $C_1$-$C_4$-haloalkyl, $C_1$-$C_4$-alkoxy-$C_1$-$C_4$-alkyl, or phenyl, which is unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups;
$R^{5a}$, $R^{5b}$, $R^{5c}$ and $R^{5d}$ are each hydrogen, or one of these radicals may also be $C_1$-$C_4$-alkyl.
$R^6$ hydrogen, $C_1$-$C_4$-alkyl, formyl, $C_1$-$C_6$-alkylcarbonyl, $C_1$-$C_4$-haloalkylcarbonyl, $C_1$-$C_6$-alkoxycarbonyl, $C_1$-$C_4$-alkoxy-$C_1$-$C_4$-alkoxycarbonyl or $C_1$-$C_6$-alkylthiocarbonyl.
$R^7$ hydrogen;

In a very preferred embodiment of the invention both radicals $R^3$ and $R^4$ are hydrogen. In another preferred embodiment of the invention $R^3$ is hydrogen and $R^4$ is selected from $C_1$-$C_4$-alkyl, $C_1$-$C_4$-haloalkyl, $C_1$-$C_4$-alkoxy-$C_1$-$C_4$-alkyl, or phenyl, which is unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_8$-haloalkoxy groups. In this embodiment $R^4$ is preferably methyl, ethyl or especially unsubstituted or substituted phenyl.

A further embodiment of the present invention relates to compounds of the formula I, wherein at least one and preferably one or two of the radicals $R^{5a}$, $R^{5b}$, $R^{5c}$ and $R^{5d}$ is different from hydrogen. In this case, preference is given to compounds of the formula I wherein 1 or 2 of the radicals $R^{5a}$, $R^{5b}$, $R^{5c}$ or $R^{5d}$ are selected from alkyl, optionally substituted phenyl or optionally substituted benzyl.

Amongst compounds I, preference is given to those wherein A is a radical of formula $A^2$, in particular compounds of the formula I with A being $A^2$, wherein $R^7$ is =H. These compounds are tautomers of the compounds of formula I with A being $A^1$, wherein $R^6$ is hydrogen. These tautomers are present as their equilibrium mixture.

Amongst compounds of the formula I, preference is given to the following compounds of the formula I-A, wherein A is a radical $A^2$ with X being O:

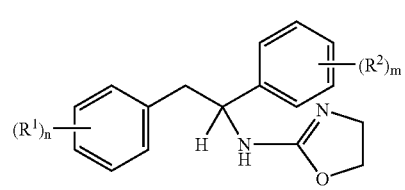

(I-A)

wherein the variables n, m, $R^1$ and $R^2$ have the meanings given above. Examples of these compounds are those wherein $(R^1)_n$ and $(R^2)_m$ have the meanings given in each line of table A (Compounds I-A.1 to I-A.1347). In table A the number infront of the radical indicates its position on the phenyl ring.

TABEL A

|  | $(R^1)_n$ | $(R^2)_m$ |
|---|---|---|
| A-1 | — | — |
| A-2 | 2-Cl | — |
| A-3 | 2-F | — |
| A-4 | 2-Br | — |
| A-5 | 2-OCH$_3$ | — |
| A-6 | 2-CF$_3$ | — |
| A-7 | 2-C$_6$H$_5$ | — |
| A-8 | 2-CH$_3$ | — |
| A-9 | 3-Cl | — |
| A-10 | 3-F | — |
| A-11 | 3-Br | — |
| A-12 | 3-OCH$_3$ | — |
| A-13 | 3-CF$_3$ | — |
| A-14 | 3-C$_6$H$_5$ | — |
| A-15 | 3-CH$_3$ | — |
| A-16 | 4-Cl | — |
| A-17 | 4-F | — |
| A-18 | 4-Br | — |
| A-19 | 4-OCH$_3$ | — |
| A-20 | 4-CF$_3$ | — |
| A-21 | 4-C$_6$H$_5$ | — |
| A-22 | 4-CH$_3$ | — |
| A-23 | 2-Cl, 6-Cl | — |
| A-24 | 2-Cl, 5-Cl | — |

TABEL A-continued

| | $(R^1)_n$ | $(R^2)_m$ |
|---|---|---|
| A-25 | 2-Cl, 3-Cl | — |
| A-26 | 2-Cl, 4-Cl | — |
| A-27 | 3-Cl, 4-Cl | — |
| A-28 | 3-Cl, 5-Cl | — |
| A-29 | 2-F, 6-F | — |
| A-30 | 2-F, 5-F | — |
| A-31 | 2-F, 3-F | — |
| A-32 | 2-F, 4-F | — |
| A-33 | 3-F, 4-F | — |
| A-34 | 3-F, 5-F | — |
| A-35 | 2-F, 6-Cl | — |
| A-36 | 2-F, 5-Cl | — |
| A-37 | 2-F, 3-Cl | — |
| A-38 | 2-F, 4-Cl | — |
| A-39 | 3-F, 4-Cl | — |
| A-40 | 3-F, 5-Cl | — |
| A-41 | 2-Cl, 6-F | — |
| A-42 | 2-Cl, 5-F | — |
| A-43 | 2-Cl, 3-F | — |
| A-44 | 2-Cl, 4-F | — |
| A-45 | 3-Cl, 4-F | — |
| A-46 | 3-OCH$_3$, 5-Cl | — |
| A-47 | 3-OCH$_3$, 4-Cl | — |
| A-48 | 3-OCH$_3$, 2-Cl | — |
| A-49 | 4-OCH$_3$, 3-Cl | — |
| A-50 | 4-OCH$_3$, 2-Cl | — |
| A-51 | 2-OCH$_3$, 3-Cl | — |
| A-52 | 2-OCH$_3$, 4-Cl | — |
| A-53 | 2-OCH$_3$, 5-Cl | — |
| A-54 | 2-OCH$_3$, 6-Cl | — |
| A-55 | 2-OCH$_3$, 5-OCH$_3$ | — |
| A-56 | 2-OCH$_3$, 4-OCH$_3$ | — |
| A-57 | 2-OCH$_3$, 3-OCH$_3$ | — |
| A-58 | 2-OCH$_3$, 6-OCH$_3$ | — |
| A-59 | 3-OCH$_3$, 5-OCH$_3$ | — |
| A-60 | 3-OCH$_3$, 4-OCH$_3$ | — |
| A-61 | 2-Cl | 2-Cl |
| A-62 | 2-F | 2-Cl |
| A-63 | 2-Br | 2-Cl |
| A-64 | 2-OCH$_3$ | 2-Cl |
| A-65 | 2-CF$_3$ | 2-Cl |
| A-66 | 2-C$_6$H$_5$ | 2-Cl |
| A-67 | 2-CH$_3$ | 2-Cl |
| A-68 | 3-Cl | 2-Cl |
| A-69 | 3-F | 2-Cl |
| A-70 | 3-Br | 2-Cl |
| A-71 | 3-OCH$_3$ | 2-Cl |
| A-72 | 3-CF$_3$ | 2-Cl |
| A-73 | 3-C$_6$H$_5$ | 2-Cl |
| A-74 | 3-CH$_3$ | 2-Cl |
| A-75 | 4-Cl | 2-Cl |
| A-76 | 4-F | 2-Cl |
| A-77 | 4-Br | 2-Cl |
| A-78 | 4-OCH$_3$ | 2-Cl |
| A-79 | 4-CF$_3$ | 2-Cl |
| A-80 | 4-C$_6$H$_5$ | 2-Cl |
| A-81 | 4-CH$_3$ | 2-Cl |
| A-82 | 2-Cl, 6-Cl | 2-Cl |
| A-83 | 2-Cl, 5-Cl | 2-Cl |
| A-84 | 2-Cl, 3-Cl | 2-Cl |
| A-85 | 2-Cl, 4-Cl | 2-Cl |
| A-86 | 3-Cl, 4-Cl | 2-Cl |
| A-87 | 3-Cl, 5-Cl | 2-Cl |
| A-88 | 2-F, 6-F | 2-Cl |
| A-89 | 2-F, 5-F | 2-Cl |
| A-90 | 2-F, 3-F | 2-Cl |
| A-91 | 2-F, 4-F | 2-Cl |
| A-92 | 3-F, 4-F | 2-Cl |
| A-93 | 3-F, 5-F | 2-Cl |
| A-94 | 2-F, 6-Cl | 2-Cl |
| A-95 | 2-F, 5-Cl | 2-Cl |
| A-96 | 2-F, 3-Cl | 2-Cl |
| A-97 | 2-F, 4-Cl | 2-Cl |
| A-98 | 3-F, 4-Cl | 2-Cl |
| A-99 | 3-F, 5-Cl | 2-Cl |
| A-100 | 2-Cl, 6-F | 2-Cl |
| A-101 | 2-Cl, 5-F | 2-Cl |
| A-102 | 2-Cl, 3-F | 2-Cl |
| A-103 | 2-Cl, 4-F | 2-Cl |
| A-104 | 3-Cl, 4-F | 2-Cl |
| A-105 | 3-OCH$_3$, 5-Cl | 2-Cl |
| A-106 | 3-OCH$_3$, 4-Cl | 2-Cl |
| A-107 | 3-OCH$_3$, 2-Cl | 2-Cl |
| A-108 | 4-OCH$_3$, 3-Cl | 2-Cl |
| A-109 | 4-OCH$_3$, 2-Cl | 2-Cl |
| A-110 | 2-OCH$_3$, 3-Cl | 2-Cl |
| A-111 | 2-OCH$_3$, 4-Cl | 2-Cl |
| A-112 | 2-OCH$_3$, 5-Cl | 2-Cl |
| A-113 | 2-OCH$_3$, 6-Cl | 2-Cl |
| A-114 | 2-OCH$_3$, 5-OCH$_3$ | 2-Cl |
| A-115 | 2-OCH$_3$, 4-OCH$_3$ | 2-Cl |
| A-116 | 2-OCH$_3$, 3-OCH$_3$ | 2-Cl |
| A-117 | 2-OCH$_3$, 6-OCH$_3$ | 2-Cl |
| A-118 | 3-OCH$_3$, 5-OCH$_3$ | 2-Cl |
| A-119 | 3-OCH$_3$, 4-OCH$_3$ | 2-Cl |
| A-120 | — | 2-F |
| A-121 | 2-Cl | 2-F |
| A-122 | 2-F | 2-F |
| A-123 | 2-Br | 2-F |
| A-124 | 2-OCH$_3$ | 2-F |
| A-125 | 2-CF$_3$ | 2-F |
| A-126 | 2-C$_6$H$_5$ | 2-F |
| A-127 | 2-CH$_3$ | 2-F |
| A-128 | 3-Cl | 2-F |
| A-129 | 3-F | 2-F |
| A-130 | 3-Br | 2-F |
| A-131 | 3-OCH$_3$ | 2-F |
| A-132 | 3-CF$_3$ | 2-F |
| A-133 | 3-C$_6$H$_5$ | 2-F |
| A-134 | 3-CH$_3$ | 2-F |
| A-135 | 4-Cl | 2-F |
| A-136 | 4-F | 2-F |
| A-137 | 4-Br | 2-F |
| A-138 | 4-OCH$_3$ | 2-F |
| A-139 | 4-CF$_3$ | 2-F |
| A-140 | 4-C$_6$H$_5$ | 2-F |
| A-141 | 4-CH$_3$ | 2-F |
| A-142 | 2-Cl, 6-Cl | 2-F |
| A-143 | 2-Cl, 5-Cl | 2-F |
| A-144 | 2-Cl, 3-Cl | 2-F |
| A-145 | 2-Cl, 4-Cl | 2-F |
| A-146 | 3-Cl, 4-Cl | 2-F |
| A-147 | 3-Cl, 5-Cl | 2-F |
| A-148 | 2-F, 6-F | 2-F |
| A-149 | 2-F, 5-F | 2-F |
| A-150 | 2-F, 3-F | 2-F |
| A-151 | 2-F, 4-F | 2-F |
| A-152 | 3-F, 4-F | 2-F |
| A-153 | 3-F, 5-F | 2-F |
| A-154 | 2-F, 6-Cl | 2-F |
| A-155 | 2-F, 5-Cl | 2-F |
| A-156 | 2-F, 3-Cl | 2-F |
| A-157 | 2-F, 4-Cl | 2-F |
| A-158 | 3-F, 4-Cl | 2-F |
| A-159 | 3-F, 5-Cl | 2-F |
| A-160 | 2-Cl, 6-F | 2-F |
| A-161 | 2-Cl, 5-F | 2-F |
| A-162 | 2-Cl, 3-F | 2-F |
| A-163 | 2-Cl, 4-F | 2-F |
| A-164 | 3-Cl, 4-F | 2-F |
| A-165 | 3-OCH$_3$, 4-Cl | 2-F |
| A-166 | 3-OCH$_3$, 2-Cl | 2-F |
| A-167 | 4-OCH$_3$, 3-Cl | 2-F |
| A-168 | 4-OCH$_3$, 2-Cl | 2-F |
| A-169 | 2-OCH$_3$, 3-Cl | 2-F |
| A-170 | 2-OCH$_3$, 4-Cl | 2-F |
| A-171 | 2-OCH$_3$, 5-Cl | 2-F |
| A-172 | 2-OCH$_3$, 6-Cl | 2-F |
| A-173 | 2-OCH$_3$, 5-OCH$_3$ | 2-F |
| A-174 | 2-OCH$_3$, 4-OCH$_3$ | 2-F |
| A-175 | 2-OCH$_3$, 3-OCH$_3$ | 2-F |
| A-176 | 2-OCH$_3$, 6-OCH$_3$ | 2-F |
| A-177 | 3-OCH$_3$, 5-OCH$_3$ | 2-F |
| A-178 | 3-OCH$_3$, 4-OCH$_3$ | 2-F |

TABEL A-continued

| | $(R^1)_n$ | $(R^2)_m$ |
|---|---|---|
| A-179 | — | 2-Br |
| A-180 | 2-Cl | 2-Br |
| A-181 | 2-F | 2-Br |
| A-182 | 2-Br | 2-Br |
| A-183 | 2-OCH$_3$ | 2-Br |
| A-184 | 2-CF$_3$ | 2-Br |
| A-185 | 2-C$_6$H$_5$ | 2-Br |
| A-186 | 2-CH$_3$ | 2-Br |
| A-187 | 3-Cl | 2-Br |
| A-188 | 3-F | 2-Br |
| A-189 | 3-Br | 2-Br |
| A-190 | 3-OCH$_3$ | 2-Br |
| A-191 | 3-CF$_3$ | 2-Br |
| A-192 | 3-C$_6$H$_5$ | 2-Br |
| A-193 | 3-CH$_3$ | 2-Br |
| A-194 | 4-Cl | 2-Br |
| A-195 | 4-F | 2-Br |
| A-196 | 4-Br | 2-Br |
| A-197 | 4-OCH$_3$ | 2-Br |
| A-198 | 4-CF$_3$ | 2-Br |
| A-199 | 4-C$_6$H$_5$ | 2-Br |
| A-200 | 4-CH$_3$ | 2-Br |
| A-201 | 2-Cl, 6-Cl | 2-Br |
| A-202 | 2-Cl, 5-Cl | 2-Br |
| A-203 | 2-Cl, 3-Cl | 2-Br |
| A-204 | 2-Cl, 4-Cl | 2-Br |
| A-205 | 3-Cl, 4-Cl | 2-Br |
| A-206 | 3-Cl, 5-Cl | 2-Br |
| A-207 | 2-F, 6-F | 2-Br |
| A-208 | 2-F, 5-F | 2-Br |
| A-209 | 2-F, 3-F | 2-Br |
| A-210 | 2-F, 4-F | 2-Br |
| A-211 | 3-F, 4-F | 2-Br |
| A-212 | 3-F, 5-F | 2-Br |
| A-213 | 2-F, 6-Cl | 2-Br |
| A-214 | 2-F, 5-Cl | 2-Br |
| A-215 | 2-F, 3-Cl | 2-Br |
| A-216 | 2-F, 4-Cl | 2-Br |
| A-217 | 3-F, 4-Cl | 2-Br |
| A-218 | 3-F, 5-Cl | 2-Br |
| A-219 | 2-Cl, 6-F | 2-Br |
| A-220 | 2-Cl, 5-F | 2-Br |
| A-221 | 2-Cl, 3-F | 2-Br |
| A-222 | 2-Cl, 4-F | 2-Br |
| A-223 | 3-Cl, 4-F | 2-Br |
| A-224 | 3-OCH$_3$, 4-Cl | 2-Br |
| A-225 | 3-OCH$_3$, 2-Cl | 2-Br |
| A-226 | 4-OCH$_3$, 3-Cl | 2-Br |
| A-227 | 4-OCH$_3$, 2-Cl | 2-Br |
| A-228 | 2-OCH$_3$, 3-Cl | 2-Br |
| A-229 | 2-OCH$_3$, 4-Cl | 2-Br |
| A-230 | 2-OCH$_3$, 5-Cl | 2-Br |
| A-231 | 2-OCH$_3$, 6-Cl | 2-Br |
| A-232 | 2-OCH$_3$, 5-OCH$_3$ | 2-Br |
| A-233 | 2-OCH$_3$, 4-OCH$_3$ | 2-Br |
| A-234 | 2-OCH$_3$, 3-OCH$_3$ | 2-Br |
| A-235 | 2-OCH$_3$, 6-OCH$_3$ | 2-Br |
| A-236 | 3-OCH$_3$, 5-OCH$_3$ | 2-Br |
| A-237 | 3-OCH$_3$, 4-OCH$_3$ | 2-Br |
| A-238 | — | 2-CH$_3$ |
| A-239 | 2-Cl | 2-CH$_3$ |
| A-240 | 2-F | 2-CH$_3$ |
| A-241 | 2-Br | 2-CH$_3$ |
| A-242 | 2-OCH$_3$ | 2-CH$_3$ |
| A-243 | 2-CF$_3$ | 2-CH$_3$ |
| A-244 | 2-C$_6$H$_5$ | 2-CH$_3$ |
| A-245 | 2-CH$_3$ | 2-CH$_3$ |
| A-246 | 3-Cl | 2-CH$_3$ |
| A-247 | 3-F | 2-CH$_3$ |
| A-248 | 3-Br | 2-CH$_3$ |
| A-249 | 3-OCH$_3$ | 2-CH$_3$ |
| A-250 | 3-CF$_3$ | 2-CH$_3$ |
| A-251 | 3-C$_6$H$_5$ | 2-CH$_3$ |
| A-252 | 3-CH$_3$ | 2-CH$_3$ |
| A-253 | 4-Cl | 2-CH$_3$ |
| A-254 | 4-F | 2-CH$_3$ |
| A-255 | 4-Br | 2-CH$_3$ |
| A-256 | 4-OCH$_3$ | 2-CH$_3$ |
| A-257 | 4-CF$_3$ | 2-CH$_3$ |
| A-258 | 4-C$_6$H$_5$ | 2-CH$_3$ |
| A-259 | 4-CH$_3$ | 2-CH$_3$ |
| A-260 | 2-Cl, 6-Cl | 2-CH$_3$ |
| A-261 | 2-Cl, 5-Cl | 2-CH$_3$ |
| A-262 | 2-Cl, 3-Cl | 2-CH$_3$ |
| A-263 | 2-Cl, 4-Cl | 2-CH$_3$ |
| A-264 | 3-Cl, 4-Cl | 2-CH$_3$ |
| A-265 | 3-Cl, 5-Cl | 2-CH$_3$ |
| A-266 | 2-F, 6-F | 2-CH$_3$ |
| A-267 | 2-F, 5-F | 2-CH$_3$ |
| A-268 | 2-F, 3-F | 2-CH$_3$ |
| A-269 | 2-F, 4-F | 2-CH$_3$ |
| A-270 | 3-F, 4-F | 2-CH$_3$ |
| A-271 | 3-F, 5-F | 2-CH$_3$ |
| A-272 | 2-F, 6-Cl | 2-CH$_3$ |
| A-273 | 2-F, 5-Cl | 2-CH$_3$ |
| A-274 | 2-F, 3-Cl | 2-CH$_3$ |
| A-275 | 2-F, 4-Cl | 2-CH$_3$ |
| A-276 | 3-F, 4-Cl | 2-CH$_3$ |
| A-277 | 3-F, 5-Cl | 2-CH$_3$ |
| A-278 | 2-Cl, 6-F | 2-CH$_3$ |
| A-279 | 2-Cl, 5-F | 2-CH$_3$ |
| A-280 | 2-Cl, 3-F | 2-CH$_3$ |
| A-281 | 2-Cl, 4-F | 2-CH$_3$ |
| A-282 | 3-Cl, 4-F | 2-CH$_3$ |
| A-283 | 3-OCH$_3$, 4-Cl | 2-CH$_3$ |
| A-284 | 3-OCH$_3$, 2-Cl | 2-CH$_3$ |
| A-285 | 4-OCH$_3$, 3-Cl | 2-CH$_3$ |
| A-286 | 4-OCH$_3$, 2-Cl | 2-CH$_3$ |
| A-287 | 2-OCH$_3$, 3-Cl | 2-CH$_3$ |
| A-288 | 2-OCH$_3$, 4-Cl | 2-CH$_3$ |
| A-289 | 2-OCH$_3$, 5-Cl | 2-CH$_3$ |
| A-290 | 2-OCH$_3$, 6-Cl | 2-CH$_3$ |
| A-291 | 2-OCH$_3$, 5-OCH$_3$ | 2-CH$_3$ |
| A-292 | 2-OCH$_3$, 4-OCH$_3$ | 2-CH$_3$ |
| A-293 | 2-OCH$_3$, 3-OCH$_3$ | 2-CH$_3$ |
| A-294 | 2-OCH$_3$, 6-OCH$_3$ | 2-CH$_3$ |
| A-295 | 3-OCH$_3$, 5-OCH$_3$ | 2-CH$_3$ |
| A-296 | 3-OCH$_3$, 4-OCH$_3$ | 2-CH$_3$ |
| A-297 | — | 2-CF$_3$ |
| A-298 | 2-Cl | 2-CF$_3$ |
| A-299 | 2-F | 2-CF$_3$ |
| A-300 | 2-Br | 2-CF$_3$ |
| A-301 | 2-OCH$_3$ | 2-CF$_3$ |
| A-302 | 2-CF$_3$ | 2-CF$_3$ |
| A-303 | 2-C$_6$H$_5$ | 2-CF$_3$ |
| A-304 | 2-CH$_3$ | 2-CF$_3$ |
| A-305 | 3-Cl | 2-CF$_3$ |
| A-306 | 3-F | 2-CF$_3$ |
| A-307 | 3-Br | 2-CF$_3$ |
| A-308 | 3-OCH$_3$ | 2-CF$_3$ |
| A-309 | 3-CF$_3$ | 2-CF$_3$ |
| A-310 | 3-C$_6$H$_5$ | 2-CF$_3$ |
| A-311 | 3-CH$_3$ | 2-CF$_3$ |
| A-312 | 4-Cl | 2-CF$_3$ |
| A-313 | 4-F | 2-CF$_3$ |
| A-314 | 4-Br | 2-CF$_3$ |
| A-315 | 4-OCH$_3$ | 2-CF$_3$ |
| A-316 | 4-CF$_3$ | 2-CF$_3$ |
| A-317 | 4-C$_6$H$_5$ | 2-CF$_3$ |
| A-318 | 4-CH$_3$ | 2-CF$_3$ |
| A-319 | 2-Cl, 6-Cl | 2-CF$_3$ |
| A-320 | 2-Cl, 5-Cl | 2-CF$_3$ |
| A-321 | 2-Cl, 3-Cl | 2-CF$_3$ |
| A-322 | 2-Cl, 4-Cl | 2-CF$_3$ |
| A-323 | 3-Cl, 4-Cl | 2-CF$_3$ |
| A-324 | 3-Cl, 5-Cl | 2-CF$_3$ |
| A-325 | 2-F, 6-F | 2-CF$_3$ |
| A-326 | 2-F, 5-F | 2-CF$_3$ |
| A-327 | 2-F, 3-F | 2-CF$_3$ |
| A-328 | 2-F, 4-F | 2-CF$_3$ |
| A-329 | 3-F, 4-F | 2-CF$_3$ |
| A-330 | 3-F, 5-F | 2-CF$_3$ |
| A-331 | 2-F, 6-Cl | 2-CF$_3$ |
| A-332 | 2-F, 5-Cl | 2-CF$_3$ |

TABEL A-continued

| | (R¹)ₙ | (R²)ₘ |
|---|---|---|
| A-333 | 2-F, 3-Cl | 2-CF₃ |
| A-334 | 2-F, 4-Cl | 2-CF₃ |
| A-335 | 3-F, 4-Cl | 2-CF₃ |
| A-336 | 3-F, 5-Cl | 2-CF₃ |
| A-337 | 2-Cl, 6-F | 2-CF₃ |
| A-338 | 2-Cl, 5-F | 2-CF₃ |
| A-339 | 2-Cl, 3-F | 2-CF₃ |
| A-340 | 2-Cl, 4-F | 2-CF₃ |
| A-341 | 3-Cl, 4-F | 2-CF₃ |
| A-342 | 3-OCH₃, 4-Cl | 2-CF₃ |
| A-343 | 3-OCH₃, 2-Cl | 2-CF₃ |
| A-344 | 4-OCH₃, 3-Cl | 2-CF₃ |
| A-345 | 4-OCH₃, 2-Cl | 2-CF₃ |
| A-346 | 2-OCH₃, 3-Cl | 2-CF₃ |
| A-347 | 2-OCH₃, 4-Cl | 2-CF₃ |
| A-348 | 2-OCH₃, 5-Cl | 2-CF₃ |
| A-349 | 2-OCH₃, 6-Cl | 2-CF₃ |
| A-350 | 2-OCH₃, 5-OCH₃ | 2-CF₃ |
| A-351 | 2-OCH₃, 4-OCH₃ | 2-CF₃ |
| A-352 | 2-OCH₃, 3-OCH₃ | 2-CF₃ |
| A-353 | 2-OCH₃, 6-OCH₃ | 2-CF₃ |
| A-354 | 3-OCH₃, 5-OCH₃ | 2-CF₃ |
| A-355 | 3-OCH₃, 4-OCH₃ | 2-CF₃ |
| A-356 | — | 2-OCH₃ |
| A-357 | 2-Cl | 2-OCH₃ |
| A-358 | 2-F | 2-OCH₃ |
| A-359 | 2-Br | 2-OCH₃ |
| A-360 | 2-OCH₃ | 2-OCH₃ |
| A-361 | 2-CF₃ | 2-OCH₃ |
| A-362 | 2-C₆H₅ | 2-OCH₃ |
| A-363 | 2-CH₃ | 2-OCH₃ |
| A-364 | 3-Cl | 2-OCH₃ |
| A-365 | 3-F | 2-OCH₃ |
| A-366 | 3-Br | 2-OCH₃ |
| A-367 | 3-OCH₃ | 2-OCH₃ |
| A-368 | 3-CF₃ | 2-OCH₃ |
| A-369 | 3-C₆H₅ | 2-OCH₃ |
| A-370 | 3-CH₃ | 2-OCH₃ |
| A-371 | 4-Cl | 2-OCH₃ |
| A-372 | 4-F | 2-OCH₃ |
| A-373 | 4-Br | 2-OCH₃ |
| A-374 | 4-OCH₃ | 2-OCH₃ |
| A-375 | 4-CF₃ | 2-OCH₃ |
| A-376 | 4-C₆H₅ | 2-OCH₃ |
| A-377 | 4-CH₃ | 2-OCH₃ |
| A-378 | 2-Cl, 6-Cl | 2-OCH₃ |
| A-379 | 2-Cl, 5-Cl | 2-OCH₃ |
| A-380 | 2-Cl, 3-Cl | 2-OCH₃ |
| A-381 | 2-Cl, 4-Cl | 2-OCH₃ |
| A-382 | 3-Cl, 4-Cl | 2-OCH₃ |
| A-383 | 3-Cl, 5-Cl | 2-OCH₃ |
| A-384 | 2-F, 6-F | 2-OCH₃ |
| A-385 | 2-F, 5-F | 2-OCH₃ |
| A-386 | 2-F, 3-F | 2-OCH₃ |
| A-387 | 2-F, 4-F | 2-OCH₃ |
| A-388 | 3-F, 4-F | 2-OCH₃ |
| A-389 | 3-F, 5-F | 2-OCH₃ |
| A-390 | 2-F, 6-Cl | 2-OCH₃ |
| A-391 | 2-F, 5-Cl | 2-OCH₃ |
| A-392 | 2-F, 3-Cl | 2-OCH₃ |
| A-393 | 2-F, 4-Cl | 2-OCH₃ |
| A-394 | 3-F, 4-Cl | 2-OCH₃ |
| A-395 | 3-F, 5-Cl | 2-OCH₃ |
| A-396 | 2-Cl, 6-F | 2-OCH₃ |
| A-397 | 2-Cl, 5-F | 2-OCH₃ |
| A-398 | 2-Cl, 3-F | 2-OCH₃ |
| A-399 | 2-Cl, 4-F | 2-OCH₃ |
| A-400 | 3-Cl, 4-F | 2-OCH₃ |
| A-401 | 3-OCH₃, 4-Cl | 2-OCH₃ |
| A-402 | 3-OCH₃, 2-Cl | 2-OCH₃ |
| A-403 | 4-OCH₃, 3-Cl | 2-OCH₃ |
| A-404 | 4-OCH₃, 2-Cl | 2-OCH₃ |
| A-405 | 2-OCH₃, 3-Cl | 2-OCH₃ |
| A-406 | 2-OCH₃, 4-Cl | 2-OCH₃ |
| A-407 | 2-OCH₃, 5-Cl | 2-OCH₃ |
| A-408 | 2-OCH₃, 6-Cl | 2-OCH₃ |
| A-409 | 2-OCH₃, 5-OCH₃ | 2-OCH₃ |
| A-410 | 2-OCH₃, 4-OCH₃ | 2-OCH₃ |
| A-411 | 2-OCH₃, 3-OCH₃ | 2-OCH₃ |
| A-412 | 2-OCH₃, 6-OCH₃ | 2-OCH₃ |
| A-413 | 3-OCH₃, 5-OCH₃ | 2-OCH₃ |
| A-414 | 3-OCH₃, 4-OCH₃ | 2-OCH₃ |
| A-415 | — | 3-Cl |
| A-416 | 2-Cl | 3-Cl |
| A-417 | 2-F | 3-Cl |
| A-418 | 2-Br | 3-Cl |
| A-419 | 2-OCH₃ | 3-Cl |
| A-420 | 2-CF₃ | 3-Cl |
| A-421 | 2-C₆H₅ | 3-Cl |
| A-422 | 2-CH₃ | 3-Cl |
| A-423 | 3-Cl | 3-Cl |
| A-424 | 3-F | 3-Cl |
| A-425 | 3-Br | 3-Cl |
| A-426 | 3-OCH₃ | 3-Cl |
| A-427 | 3-CF₃ | 3-Cl |
| A-428 | 3-C₆H₅ | 3-Cl |
| A-429 | 3-CH₃ | 3-Cl |
| A-430 | 4-Cl | 3-Cl |
| A-431 | 4-F | 3-Cl |
| A-432 | 4-Br | 3-Cl |
| A-433 | 4-OCH₃ | 3-Cl |
| A-434 | 4-CF₃ | 3-Cl |
| A-435 | 4-C₆H₅ | 3-Cl |
| A-436 | 4-CH₃ | 3-Cl |
| A-437 | 2-Cl, 6-Cl | 3-Cl |
| A-438 | 2-Cl, 5-Cl | 3-Cl |
| A-439 | 2-Cl, 3-Cl | 3-Cl |
| A-440 | 2-Cl, 4-Cl | 3-Cl |
| A-441 | 3-Cl, 4-Cl | 3-Cl |
| A-442 | 3-Cl, 5-Cl | 3-Cl |
| A-443 | 2-F, 6-F | 3-Cl |
| A-444 | 2-F, 5-F | 3-Cl |
| A-445 | 2-F, 3-F | 3-Cl |
| A-446 | 2-F, 4-F | 3-Cl |
| A-447 | 3-F, 4-F | 3-Cl |
| A-448 | 3-F, 5-F | 3-Cl |
| A-449 | 2-F, 6-Cl | 3-Cl |
| A-450 | 2-F, 5-Cl | 3-Cl |
| A-451 | 2-F, 3-Cl | 3-Cl |
| A-452 | 2-F, 4-Cl | 3-Cl |
| A-453 | 3-F, 4-Cl | 3-Cl |
| A-454 | 3-F, 5-Cl | 3-Cl |
| A-455 | 2-Cl, 6-F | 3-Cl |
| A-456 | 2-Cl, 5-F | 3-Cl |
| A-457 | 2-Cl, 3-F | 3-Cl |
| A-458 | 2-Cl, 4-F | 3-Cl |
| A-459 | 3-Cl, 4-F | 3-Cl |
| A-460 | 3-OCH₃, 4-Cl | 3-Cl |
| A-461 | 3-OCH₃, 2-Cl | 3-Cl |
| A-462 | 4-OCH₃, 3-Cl | 3-Cl |
| A-463 | 4-OCH₃, 2-Cl | 3-Cl |
| A-464 | 2-OCH₃, 3-Cl | 3-Cl |
| A-465 | 2-OCH₃, 4-Cl | 3-Cl |
| A-466 | 2-OCH₃, 5-Cl | 3-Cl |
| A-467 | 2-OCH₃, 6-Cl | 3-Cl |
| A-468 | 2-OCH₃, 5-OCH₃ | 3-Cl |
| A-469 | 2-OCH₃, 4-OCH₃ | 3-Cl |
| A-470 | 2-OCH₃, 3-OCH₃ | 3-Cl |
| A-471 | 2-OCH₃, 6-OCH₃ | 3-Cl |
| A-472 | 3-OCH₃, 5-OCH₃ | 3-Cl |
| A-473 | 3-OCH₃, 4-OCH₃ | 3-Cl |
| A-474 | — | 3-Br |
| A-475 | 2-Cl | 3-Br |
| A-476 | 2-F | 3-Br |
| A-477 | 2-Br | 3-Br |
| A-478 | 2-OCH₃ | 3-Br |
| A-479 | 2-CF₃ | 3-Br |
| A-480 | 2-C₆H₅ | 3-Br |
| A-481 | 2-CH₃ | 3-Br |
| A-482 | 3-Cl | 3-Br |
| A-483 | 3-F | 3-Br |
| A-484 | 3-Br | 3-Br |
| A-485 | 3-OCH₃ | 3-Br |
| A-486 | 3-CF₃ | 3-Br |

TABEL A-continued

| | (R¹)ₙ | (R²)ₘ |
|---|---|---|
| A-487 | 3-C₆H₅ | 3-Br |
| A-488 | 3-CH₃ | 3-Br |
| A-489 | 4-Cl | 3-Br |
| A-490 | 4-F | 3-Br |
| A-491 | 4-Br | 3-Br |
| A-492 | 4-OCH₃ | 3-Br |
| A-493 | 4-CF₃ | 3-Br |
| A-494 | 4-C₆H₅ | 3-Br |
| A-495 | 4-CH₃ | 3-Br |
| A-496 | 2-Cl, 6-Cl | 3-Br |
| A-497 | 2-Cl, 5-Cl | 3-Br |
| A-498 | 2-Cl, 3-Cl | 3-Br |
| A-499 | 2-Cl, 4-Cl | 3-Br |
| A-500 | 3-Cl, 4-Cl | 3-Br |
| A-501 | 3-Cl, 5-Cl | 3-Br |
| A-502 | 2-F, 6-F | 3-Br |
| A-503 | 2-F, 5-F | 3-Br |
| A-504 | 2-F, 3-F | 3-Br |
| A-505 | 2-F, 4-F | 3-Br |
| A-506 | 3-F, 4-F | 3-Br |
| A-507 | 3-F, 5-F | 3-Br |
| A-508 | 2-F, 6-Cl | 3-Br |
| A-509 | 2-F, 5-Cl | 3-Br |
| A-510 | 2-F, 3-Cl | 3-Br |
| A-511 | 2-F, 4-Cl | 3-Br |
| A-512 | 3-F, 4-Cl | 3-Br |
| A-513 | 3-F, 5-Cl | 3-Br |
| A-514 | 2-Cl, 6-F | 3-Br |
| A-515 | 2-Cl, 5-F | 3-Br |
| A-516 | 2-Cl, 3-F | 3-Br |
| A-517 | 2-Cl, 4-F | 3-Br |
| A-518 | 3-Cl, 4-F | 3-Br |
| A-519 | 3-OCH₃, 4-Cl | 3-Br |
| A-520 | 3-OCH₃, 2-Cl | 3-Br |
| A-521 | 4-OCH₃, 3-Cl | 3-Br |
| A-522 | 4-OCH₃, 2-Cl | 3-Br |
| A-523 | 2-OCH₃, 3-Cl | 3-Br |
| A-524 | 2-OCH₃, 4-Cl | 3-Br |
| A-525 | 2-OCH₃, 5-Cl | 3-Br |
| A-526 | 2-OCH₃, 6-Cl | 3-Br |
| A-527 | 2-OCH₃, 5-OCH₃ | 3-Br |
| A-528 | 2-OCH₃, 4-OCH₃ | 3-Br |
| A-529 | 2-OCH₃, 3-OCH₃ | 3-Br |
| A-530 | 2-OCH₃, 6-OCH₃ | 3-Br |
| A-531 | 3-OCH₃, 5-OCH₃ | 3-Br |
| A-532 | 3-OCH₃, 4-OCH₃ | 3-Br |
| A-533 | — | 3-F |
| A-534 | 2-Cl | 3-F |
| A-535 | 2-F | 3-F |
| A-536 | 2-Br | 3-F |
| A-537 | 2-OCH₃ | 3-F |
| A-538 | 2-CF₃ | 3-F |
| A-539 | 2-C₆H₅ | 3-F |
| A-540 | 2-CH₃ | 3-F |
| A-541 | 3-Cl | 3-F |
| A-542 | 3-F | 3-F |
| A-543 | 3-Br | 3-F |
| A-544 | 3-OCH₃ | 3-F |
| A-545 | 3-CF₃ | 3-F |
| A-546 | 3-C₆H₅ | 3-F |
| A-547 | 3-CH₃ | 3-F |
| A-548 | 4-Cl | 3-F |
| A-549 | 4-F | 3-F |
| A-550 | 4-Br | 3-F |
| A-551 | 4-OCH₃ | 3-F |
| A-552 | 4-CF₃ | 3-F |
| A-553 | 4-C₆H₅ | 3-F |
| A-554 | 4-CH₃ | 3-F |
| A-555 | 2-Cl, 6-Cl | 3-F |
| A-556 | 2-Cl, 5-Cl | 3-F |
| A-557 | 2-Cl, 3-Cl | 3-F |
| A-558 | 2-Cl, 4-Cl | 3-F |
| A-559 | 3-Cl, 4-Cl | 3-F |
| A-560 | 3-Cl, 5-Cl | 3-F |
| A-561 | 2-F, 6-F | 3-F |
| A-562 | 2-F, 5-F | 3-F |
| A-563 | 2-F, 3-F | 3-F |
| A-564 | 2-F, 4-F | 3-F |
| A-565 | 3-F, 4-F | 3-F |
| A-566 | 3-F, 5-F | 3-F |
| A-567 | 2-F, 6-Cl | 3-F |
| A-568 | 2-F, 5-Cl | 3-F |
| A-569 | 2-F, 3-Cl | 3-F |
| A-570 | 2-F, 4-Cl | 3-F |
| A-571 | 3-F, 4-Cl | 3-F |
| A-572 | 3-F, 5-Cl | 3-F |
| A-573 | 2-Cl, 6-F | 3-F |
| A-574 | 2-Cl, 5-F | 3-F |
| A-575 | 2-Cl, 3-F | 3-F |
| A-576 | 2-Cl, 4-F | 3-F |
| A-577 | 3-Cl, 4-F | 3-F |
| A-578 | 3-OCH₃, 4-Cl | 3-F |
| A-579 | 3-OCH₃, 2-Cl | 3-F |
| A-580 | 4-OCH₃, 3-Cl | 3-F |
| A-581 | 4-OCH₃, 2-Cl | 3-F |
| A-582 | 2-OCH₃, 3-Cl | 3-F |
| A-583 | 2-OCH₃, 4-Cl | 3-F |
| A-584 | 2-OCH₃, 5-Cl | 3-F |
| A-585 | 2-OCH₃, 6-Cl | 3-F |
| A-586 | 2-OCH₃, 5-OCH₃ | 3-F |
| A-587 | 2-OCH₃, 4-OCH₃ | 3-F |
| A-588 | 2-OCH₃, 3-OCH₃ | 3-F |
| A-589 | 2-OCH₃, 6-OCH₃ | 3-F |
| A-590 | 3-OCH₃, 5-OCH₃ | 3-F |
| A-591 | 3-OCH₃, 4-OCH₃ | 3-F |
| A-592 | — | 3-F |
| A-593 | 2-Cl | 3-CH₃ |
| A-594 | 2-F | 3-CH₃ |
| A-595 | 2-Br | 3-CH₃ |
| A-596 | 2-OCH₃ | 3-CH₃ |
| A-597 | 2-CF₃ | 3-CH₃ |
| A-598 | 2-C₆H₅ | 3-CH₃ |
| A-599 | 2-CH₃ | 3-CH₃ |
| A-600 | 3-Cl | 3-CH₃ |
| A-601 | 3-F | 3-CH₃ |
| A-602 | 3-Br | 3-CH₃ |
| A-603 | 3-OCH₃ | 3-CH₃ |
| A-604 | 3-CF₃ | 3-CH₃ |
| A-605 | 3-C₆H₅ | 3-CH₃ |
| A-606 | 3-CH₃ | 3-CH₃ |
| A-607 | 4-Cl | 3-CH₃ |
| A-608 | 4-F | 3-CH₃ |
| A-609 | 4-Br | 3-CH₃ |
| A-610 | 4-OCH₃ | 3-CH₃ |
| A-611 | 4-CF₃ | 3-CH₃ |
| A-612 | 4-C₆H₅ | 3-CH₃ |
| A-613 | 4-CH₃ | 3-CH₃ |
| A-614 | 2-Cl, 6-Cl | 3-CH₃ |
| A-615 | 2-Cl, 5-Cl | 3-CH₃ |
| A-616 | 2-Cl, 3-Cl | 3-CH₃ |
| A-617 | 2-Cl, 4-Cl | 3-CH₃ |
| A-618 | 3-Cl, 4-Cl | 3-CH₃ |
| A-619 | 3-Cl, 5-Cl | 3-CH₃ |
| A-620 | 2-F, 6-F | 3-CH₃ |
| A-621 | 2-F, 5-F | 3-CH₃ |
| A-622 | 2-F, 3-F | 3-CH₃ |
| A-623 | 2-F, 4-F | 3-CH₃ |
| A-624 | 3-F, 4-F | 3-CH₃ |
| A-625 | 3-F, 5-F | 3-CH₃ |
| A-626 | 2-F, 6-Cl | 3-CH₃ |
| A-627 | 2-F, 5-Cl | 3-CH₃ |
| A-628 | 2-F, 3-Cl | 3-CH₃ |
| A-629 | 2-F, 4-Cl | 3-CH₃ |
| A-630 | 3-F, 4-Cl | 3-CH₃ |
| A-631 | 3-F, 5-Cl | 3-CH₃ |
| A-632 | 2-Cl, 6-F | 3-CH₃ |
| A-633 | 2-Cl, 5-F | 3-CH₃ |
| A-634 | 2-Cl, 3-F | 3-CH₃ |
| A-635 | 2-Cl, 4-F | 3-CH₃ |
| A-636 | 3-Cl, 4-F | 3-CH₃ |
| A-637 | 3-OCH₃, 4-Cl | 3-CH₃ |
| A-638 | 3-OCH₃, 2-Cl | 3-CH₃ |
| A-639 | 4-OCH₃, 3-Cl | 3-CH₃ |
| A-640 | 4-OCH₃, 2-Cl | 3-CH₃ |

TABEL A-continued

| | (R¹)ₙ | (R²)ₘ |
|---|---|---|
| A-641 | 2-OCH₃, 3-Cl | 3-CH₃ |
| A-642 | 2-OCH₃, 4-Cl | 3-CH₃ |
| A-643 | 2-OCH₃, 5-Cl | 3-CH₃ |
| A-644 | 2-OCH₃, 6-Cl | 3-CH₃ |
| A-645 | 2-OCH₃, 5-OCH₃ | 3-CH₃ |
| A-646 | 2-OCH₃, 4-OCH₃ | 3-CH₃ |
| A-647 | 2-OCH₃, 3-OCH₃ | 3-CH₃ |
| A-648 | 2-OCH₃, 6-OCH₃ | 3-CH₃ |
| A-649 | 3-OCH₃, 5-OCH₃ | 3-CH₃ |
| A-650 | 3-OCH₃, 4-OCH₃ | 3-CH₃ |
| A-651 | — | 3-CF₃ |
| A-652 | 2-Cl | 3-CF₃ |
| A-653 | 2-F | 3-CF₃ |
| A-654 | 2-Br | 3-CF₃ |
| A-655 | 2-OCH₃ | 3-CF₃ |
| A-656 | 2-CF₃ | 3-CF₃ |
| A-657 | 2-C₆H₅ | 3-CF₃ |
| A-658 | 2-CH₃ | 3-CF₃ |
| A-659 | 3-Cl | 3-CF₃ |
| A-660 | 3-F | 3-CF₃ |
| A-661 | 3-Br | 3-CF₃ |
| A-662 | 3-OCH₃ | 3-CF₃ |
| A-663 | 3-CF₃ | 3-CF₃ |
| A-664 | 3-C₆H₅ | 3-CF₃ |
| A-665 | 3-CH₃ | 3-CF₃ |
| A-666 | 4-Cl | 3-CF₃ |
| A-667 | 4-F | 3-CF₃ |
| A-668 | 4-Br | 3-CF₃ |
| A-669 | 4-OCH₃ | 3-CF₃ |
| A-670 | 4-CF₃ | 3-CF₃ |
| A-671 | 4-C₆H₅ | 3-CF₃ |
| A-672 | 4-CH₃ | 3-CF₃ |
| A-673 | 2-Cl, 6-Cl | 3-CF₃ |
| A-674 | 2-Cl, 5-Cl | 3-CF₃ |
| A-675 | 2-Cl, 3-Cl | 3-CF₃ |
| A-676 | 2-Cl, 4-Cl | 3-CF₃ |
| A-677 | 3-Cl, 4-Cl | 3-CF₃ |
| A-678 | 3-Cl, 5-Cl | 3-CF₃ |
| A-679 | 2-F, 6-F | 3-CF₃ |
| A-680 | 2-F, 5-F | 3-CF₃ |
| A-681 | 2-F, 3-F | 3-CF₃ |
| A-682 | 2-F, 4-F | 3-CF₃ |
| A-683 | 3-F, 4-F | 3-CF₃ |
| A-684 | 3-F, 5-F | 3-CF₃ |
| A-685 | 2-F, 6-Cl | 3-CF₃ |
| A-686 | 2-F, 5-Cl | 3-CF₃ |
| A-687 | 2-F, 3-Cl | 3-CF₃ |
| A-688 | 2-F, 4-Cl | 3-CF₃ |
| A-689 | 3-F, 4-Cl | 3-CF₃ |
| A-690 | 3-F, 5-Cl | 3-CF₃ |
| A-691 | 2-Cl, 6-F | 3-CF₃ |
| A-692 | 2-Cl, 5-F | 3-CF₃ |
| A-693 | 2-Cl, 3-F | 3-CF₃ |
| A-694 | 2-Cl, 4-F | 3-CF₃ |
| A-695 | 3-Cl, 4-F | 3-CF₃ |
| A-696 | 3-OCH₃, 4-Cl | 3-CF₃ |
| A-697 | 3-OCH₃, 2-Cl | 3-CF₃ |
| A-698 | 4-OCH₃, 3-Cl | 3-CF₃ |
| A-699 | 4-OCH₃, 2-Cl | 3-CF₃ |
| A-700 | 2-OCH₃, 3-Cl | 3-CF₃ |
| A-701 | 2-OCH₃, 4-Cl | 3-CF₃ |
| A-702 | 2-OCH₃, 5-Cl | 3-CF₃ |
| A-703 | 2-OCH₃, 6-Cl | 3-CF₃ |
| A-704 | 2-OCH₃, 5-OCH₃ | 3-CF₃ |
| A-705 | 2-OCH₃, 4-OCH₃ | 3-CF₃ |
| A-706 | 2-OCH₃, 3-OCH₃ | 3-CF₃ |
| A-707 | 2-OCH₃, 6-OCH₃ | 3-CF₃ |
| A-708 | 3-OCH₃, 5-OCH₃ | 3-CF₃ |
| A-709 | 3-OCH₃, 4-OCH₃ | 3-CF₃ |
| A-710 | — | 3-OCH₃ |
| A-711 | 2-Cl | 3-OCH₃ |
| A-712 | 2-F | 3-OCH₃ |
| A-713 | 2-Br | 3-OCH₃ |
| A-714 | 2-OCH₃ | 3-OCH₃ |
| A-715 | 2-CF₃ | 3-OCH₃ |
| A-716 | 2-C₆H₅ | 3-OCH₃ |
| A-717 | 2-CH₃ | 3-OCH₃ |
| A-718 | 3-Cl | 3-OCH₃ |
| A-719 | 3-F | 3-OCH₃ |
| A-720 | 3-Br | 3-OCH₃ |
| A-721 | 3-OCH₃ | 3-OCH₃ |
| A-722 | 3-CF₃ | 3-OCH₃ |
| A-723 | 3-C₆H₅ | 3-OCH₃ |
| A-724 | 3-CH₃ | 3-OCH₃ |
| A-725 | 4-Cl | 3-OCH₃ |
| A-726 | 4-F | 3-OCH₃ |
| A-727 | 4-Br | 3-OCH₃ |
| A-728 | 4-OCH₃ | 3-OCH₃ |
| A-729 | 4-CF₃ | 3-OCH₃ |
| A-730 | 4-C₆H₅ | 3-OCH₃ |
| A-731 | 4-CH₃ | 3-OCH₃ |
| A-732 | 2-Cl, 6-Cl | 3-OCH₃ |
| A-733 | 2-Cl, 5-Cl | 3-OCH₃ |
| A-734 | 2-Cl, 3-Cl | 3-OCH₃ |
| A-735 | 2-Cl, 4-Cl | 3-OCH₃ |
| A-736 | 3-Cl, 4-Cl | 3-OCH₃ |
| A-737 | 3-Cl, 5-Cl | 3-OCH₃ |
| A-738 | 2-F, 6-F | 3-OCH₃ |
| A-739 | 2-F, 5-F | 3-OCH₃ |
| A-740 | 2-F, 3-F | 3-OCH₃ |
| A-741 | 2-F, 4-F | 3-OCH₃ |
| A-742 | 3-F, 4-F | 3-OCH₃ |
| A-743 | 3-F, 5-F | 3-OCH₃ |
| A-744 | 2-F, 6-Cl | 3-OCH₃ |
| A-745 | 2-F, 5-Cl | 3-OCH₃ |
| A-746 | 2-F, 3-Cl | 3-OCH₃ |
| A-747 | 2-F, 4-Cl | 3-OCH₃ |
| A-748 | 3-F, 4-Cl | 3-OCH₃ |
| A-749 | 3-F, 5-Cl | 3-OCH₃ |
| A-750 | 2-Cl, 6-F | 3-OCH₃ |
| A-751 | 2-Cl, 5-F | 3-OCH₃ |
| A-752 | 2-Cl, 3-F | 3-OCH₃ |
| A-753 | 2-Cl, 4-F | 3-OCH₃ |
| A-754 | 3-Cl, 4-F | 3-OCH₃ |
| A-755 | 3-OCH₃, 5-OCH₃ | 3-OCH₃ |
| A-756 | 3-OCH₃, 4-OCH₃ | 3-OCH₃ |
| A-757 | — | 4-Cl |
| A-758 | 2-Cl | 4-Cl |
| A-759 | 2-F | 4-Cl |
| A-760 | 2-Br | 4-Cl |
| A-761 | 2-OCH₃ | 4-Cl |
| A-762 | 2-CF₃ | 4-Cl |
| A-763 | 2-C₆H₅ | 4-Cl |
| A-764 | 2-CH₃ | 4-Cl |
| A-765 | 3-Cl | 4-Cl |
| A-766 | 3-F | 4-Cl |
| A-767 | 3-Br | 4-Cl |
| A-768 | 3-OCH₃ | 4-Cl |
| A-769 | 3-CF₃ | 4-Cl |
| A-770 | 3-C₆H₅ | 4-Cl |
| A-771 | 3-CH₃ | 4-Cl |
| A-772 | 4-Cl | 4-Cl |
| A-773 | 4-F | 4-Cl |
| A-774 | 4-Br | 4-Cl |
| A-775 | 4-OCH₃ | 4-Cl |
| A-776 | 4-CF₃ | 4-Cl |
| A-777 | 4-C₆H₅ | 4-Cl |
| A-778 | 4-CH₃ | 4-Cl |
| A-779 | 2-Cl, 6-Cl | 4-Cl |
| A-780 | 2-Cl, 5-Cl | 4-Cl |
| A-781 | 2-Cl, 3-Cl | 4-Cl |
| A-782 | 2-Cl, 4-Cl | 4-Cl |
| A-783 | 3-Cl, 4-Cl | 4-Cl |
| A-784 | 3-Cl, 5-Cl | 4-Cl |
| A-785 | 2-F, 6-F | 4-Cl |
| A-786 | 2-F, 5-F | 4-Cl |
| A-787 | 2-F, 3-F | 4-Cl |
| A-788 | 2-F, 4-F | 4-Cl |
| A-789 | 3-F, 4-F | 4-Cl |
| A-790 | 3-F, 5-F | 4-Cl |
| A-791 | 2-F, 6-Cl | 4-Cl |
| A-792 | 2-F, 5-Cl | 4-Cl |
| A-793 | 2-F, 3-Cl | 4-Cl |
| A-794 | 2-F, 4-Cl | 4-Cl |

TABEL A-continued

| | $(R^1)_n$ | $(R^2)_m$ |
|---|---|---|
| A-795 | 3-F, 4-Cl | 4-Cl |
| A-796 | 3-F, 5-Cl | 4-Cl |
| A-797 | 2-Cl, 6-F | 4-Cl |
| A-798 | 2-Cl, 5-F | 4-Cl |
| A-799 | 2-Cl, 3-F | 4-Cl |
| A-800 | 2-Cl, 4-F | 4-Cl |
| A-801 | 3-Cl, 4-F | 4-Cl |
| A-802 | 3-OCH$_3$, 4-Cl | 4-Cl |
| A-803 | 3-OCH$_3$, 2-Cl | 4-Cl |
| A-804 | 4-OCH$_3$, 3-Cl | 4-Cl |
| A-805 | 4-OCH$_3$, 2-Cl | 4-Cl |
| A-806 | 2-OCH$_3$, 3-Cl | 4-Cl |
| A-807 | 2-OCH$_3$, 4-Cl | 4-Cl |
| A-808 | 2-OCH$_3$, 5-Cl | 4-Cl |
| A-809 | 2-OCH$_3$, 6-Cl | 4-Cl |
| A-810 | 2-OCH$_3$, 5-OCH$_3$ | 4-Cl |
| A-811 | 2-OCH$_3$, 4-OCH$_3$ | 4-Cl |
| A-812 | 2-OCH$_3$, 3-OCH$_3$ | 4-Cl |
| A-813 | 2-OCH$_3$, 6-OCH$_3$ | 4-Cl |
| A-814 | 3-OCH$_3$, 5-OCH$_3$ | 4-Cl |
| A-815 | 3-OCH$_3$, 4-OCH$_3$ | 4-Cl |
| A-816 | — | 4-F |
| A-817 | 2-Cl | 4-F |
| A-818 | 2-F | 4-F |
| A-819 | 2-Br | 4-F |
| A-820 | 2-OCH$_3$ | 4-F |
| A-821 | 2-CF$_3$ | 4-F |
| A-822 | 2-C$_6$H$_5$ | 4-F |
| A-823 | 2-CH$_3$ | 4-F |
| A-824 | 3-Cl | 4-F |
| A-825 | 3-F | 4-F |
| A-826 | 3-Br | 4-F |
| A-827 | 3-OCH$_3$ | 4-F |
| A-828 | 3-CF$_3$ | 4-F |
| A-829 | 3-C$_6$H$_5$ | 4-F |
| A-830 | 3-CH$_3$ | 4-F |
| A-831 | 4-Cl | 4-F |
| A-832 | 4-F | 4-F |
| A-833 | 4-Br | 4-F |
| A-834 | 4-OCH$_3$ | 4-F |
| A-835 | 4-CF$_3$ | 4-F |
| A-836 | 4-C$_6$H$_5$ | 4-F |
| A-837 | 4-CH$_3$ | 4-F |
| A-838 | 2-Cl, 6-Cl | 4-F |
| A-839 | 2-Cl, 5-Cl | 4-F |
| A-840 | 2-Cl, 3-Cl | 4-F |
| A-841 | 2-Cl, 4-Cl | 4-F |
| A-842 | 3-Cl, 4-Cl | 4-F |
| A-843 | 3-Cl, 5-Cl | 4-F |
| A-844 | 2-F, 6-F | 4-F |
| A-845 | 2-F, 5-F | 4-F |
| A-846 | 2-F, 3-F | 4-F |
| A-847 | 2-F, 4-F | 4-F |
| A-848 | 3-F, 4-F | 4-F |
| A-849 | 3-F, 5-F | 4-F |
| A-850 | 2-F, 6-Cl | 4-F |
| A-851 | 2-F, 5-Cl | 4-F |
| A-852 | 2-F, 3-Cl | 4-F |
| A-853 | 2-F, 4-Cl | 4-F |
| A-854 | 3-F, 4-Cl | 4-F |
| A-855 | 3-F, 5-Cl | 4-F |
| A-856 | 2-Cl, 6-F | 4-F |
| A-857 | 2-Cl, 5-F | 4-F |
| A-858 | 2-Cl, 3-F | 4-F |
| A-859 | 2-Cl, 4-F | 4-F |
| A-860 | 3-Cl, 4-F | 4-F |
| A-861 | 3-OCH$_3$, 4-Cl | 4-F |
| A-862 | 3-OCH$_3$, 2-Cl | 4-F |
| A-863 | 4-OCH$_3$, 3-Cl | 4-F |
| A-864 | 4-OCH$_3$, 2-Cl | 4-F |
| A-865 | 2-OCH$_3$, 3-Cl | 4-F |
| A-866 | 2-OCH$_3$, 4-Cl | 4-F |
| A-867 | 2-OCH$_3$, 5-Cl | 4-F |
| A-868 | 2-OCH$_3$, 6-Cl | 4-F |
| A-869 | 2-OCH$_3$, 5-OCH$_3$ | 4-F |
| A-870 | 2-OCH$_3$, 4-OCH$_3$ | 4-F |
| A-871 | 2-OCH$_3$, 3-OCH$_3$ | 4-F |
| A-872 | 2-OCH$_3$, 6-OCH$_3$ | 4-F |
| A-873 | 3-OCH$_3$, 5-OCH$_3$ | 4-F |
| A-874 | 3-OCH$_3$, 4-OCH$_3$ | 4-F |
| A-875 | — | 4-OCH$_3$ |
| A-876 | 2-Cl | 4-OCH$_3$ |
| A-877 | 2-F | 4-OCH$_3$ |
| A-878 | 2-Br | 4-OCH$_3$ |
| A-879 | 2-OCH$_3$ | 4-OCH$_3$ |
| A-880 | 2-CF$_3$ | 4-OCH$_3$ |
| A-881 | 2-C$_6$H$_5$ | 4-OCH$_3$ |
| A-882 | 2-CH$_3$ | 4-OCH$_3$ |
| A-883 | 3-Cl | 4-OCH$_3$ |
| A-884 | 3-F | 4-OCH$_3$ |
| A-885 | 3-Br | 4-OCH$_3$ |
| A-886 | 3-OCH$_3$ | 4-OCH$_3$ |
| A-887 | 3-CF$_3$ | 4-OCH$_3$ |
| A-888 | 3-C$_6$H$_5$ | 4-OCH$_3$ |
| A-889 | 3-CH$_3$ | 4-OCH$_3$ |
| A-890 | 4-Cl | 4-OCH$_3$ |
| A-891 | 4-F | 4-OCH$_3$ |
| A-892 | 4-Br | 4-OCH$_3$ |
| A-893 | 4-OCH$_3$ | 4-OCH$_3$ |
| A-894 | 4-CF$_3$ | 4-OCH$_3$ |
| A-895 | 4-C$_6$H$_5$ | 4-OCH$_3$ |
| A-896 | 4-CH$_3$ | 4-OCH$_3$ |
| A-897 | 2-Cl, 6-Cl | 4-OCH$_3$ |
| A-898 | 2-Cl, 5-Cl | 4-OCH$_3$ |
| A-899 | 2-Cl, 3-Cl | 4-OCH$_3$ |
| A-900 | 2-Cl, 4-Cl | 4-OCH$_3$ |
| A-901 | 3-Cl, 4-Cl | 4-OCH$_3$ |
| A-902 | 3-Cl, 5-Cl | 4-OCH$_3$ |
| A-903 | 2-F, 6-F | 4-OCH$_3$ |
| A-904 | 2-F, 5-F | 4-OCH$_3$ |
| A-905 | 2-F, 3-F | 4-OCH$_3$ |
| A-906 | 2-F, 4-F | 4-OCH$_3$ |
| A-907 | 3-F, 4-F | 4-OCH$_3$ |
| A-908 | 3-F, 5-F | 4-OCH$_3$ |
| A-909 | 2-F, 6-Cl | 4-OCH$_3$ |
| A-910 | 2-F, 5-Cl | 4-OCH$_3$ |
| A-911 | 2-F, 3-Cl | 4-OCH$_3$ |
| A-912 | 2-F, 4-Cl | 4-OCH$_3$ |
| A-913 | 3-F, 4-Cl | 4-OCH$_3$ |
| A-914 | 3-F, 5-Cl | 4-OCH$_3$ |
| A-915 | 2-Cl, 6-F | 4-OCH$_3$ |
| A-916 | 2-Cl, 5-F | 4-OCH$_3$ |
| A-917 | 2-Cl, 3-F | 4-OCH$_3$ |
| A-918 | 2-Cl, 4-F | 4-OCH$_3$ |
| A-919 | 3-Cl, 4-F | 4-OCH$_3$ |
| A-920 | 3-OCH$_3$, 5-OCH$_3$ | 4-OCH$_3$ |
| A-921 | 3-OCH$_3$, 4-OCH$_3$ | 4-OCH$_3$ |
| A-922 | — | 4-CH$_3$ |
| A-923 | 2-Cl | 4-CH$_3$ |
| A-924 | 2-F | 4-CH$_3$ |
| A-925 | 2-Br | 4-CH$_3$ |
| A-926 | 2-OCH$_3$ | 4-CH$_3$ |
| A-927 | 2-CF$_3$ | 4-CH$_3$ |
| A-928 | 2-C$_6$H$_5$ | 4-CH$_3$ |
| A-929 | 2-CH$_3$ | 4-CH$_3$ |
| A-930 | 3-Cl | 4-CH$_3$ |
| A-931 | 3-F | 4-CH$_3$ |
| A-932 | 3-Br | 4-CH$_3$ |
| A-933 | 3-OCH$_3$ | 4-CH$_3$ |
| A-934 | 3-CF$_3$ | 4-CH$_3$ |
| A-935 | 3-C$_6$H$_5$ | 4-CH$_3$ |
| A-936 | 3-CH$_3$ | 4-CH$_3$ |
| A-937 | 4-Cl | 4-CH$_3$ |
| A-938 | 4-F | 4-CH$_3$ |
| A-939 | 4-Br | 4-CH$_3$ |
| A-940 | 4-OCH$_3$ | 4-CH$_3$ |
| A-941 | 4-CF$_3$ | 4-CH$_3$ |
| A-942 | 4-C$_6$H$_5$ | 4-CH$_3$ |
| A-943 | 4-CH$_3$ | 4-CH$_3$ |
| A-944 | 2-Cl, 6-Cl | 4-CH$_3$ |
| A-945 | 2-Cl, 5-Cl | 4-CH$_3$ |
| A-946 | 2-Cl, 3-Cl | 4-CH$_3$ |
| A-947 | 2-Cl, 4-Cl | 4-CH$_3$ |
| A-948 | 3-Cl, 4-Cl | 4-CH$_3$ |

TABEL A-continued

| | $(R^1)_n$ | $(R^2)_m$ |
|---|---|---|
| A-949 | 3-Cl, 5-Cl | 4-CH$_3$ |
| A-950 | 2-F, 6-F | 4-CH$_3$ |
| A-951 | 2-F, 5-F | 4-CH$_3$ |
| A-952 | 2-F, 3-F | 4-CH$_3$ |
| A-953 | 2-F, 4-F | 4-CH$_3$ |
| A-954 | 3-F, 4-F | 4-CH$_3$ |
| A-955 | 3-F, 5-F | 4-CH$_3$ |
| A-956 | 2-F, 6-Cl | 4-CH$_3$ |
| A-957 | 2-F, 5-Cl | 4-CH$_3$ |
| A-958 | 2-F, 3-Cl | 4-CH$_3$ |
| A-959 | 2-F, 4-Cl | 4-CH$_3$ |
| A-960 | 3-F, 4-Cl | 4-CH$_3$ |
| A-961 | 3-F, 5-Cl | 4-CH$_3$ |
| A-962 | 2-Cl, 6-F | 4-CH$_3$ |
| A-963 | 2-Cl, 5-F | 4-CH$_3$ |
| A-964 | 2-Cl, 3-F | 4-CH$_3$ |
| A-965 | 2-Cl, 4-F | 4-CH$_3$ |
| A-966 | 3-Cl, 4-F | 4-CH$_3$ |
| A-967 | 3-OCH$_3$, 4-Cl | 4-CH$_3$ |
| A-968 | 3-OCH$_3$, 2-Cl | 4-CH$_3$ |
| A-969 | 4-OCH$_3$, 3-Cl | 4-CH$_3$ |
| A-970 | 4-OCH$_3$, 2-Cl | 4-CH$_3$ |
| A-971 | 2-OCH$_3$, 3-Cl | 4-CH$_3$ |
| A-972 | 2-OCH$_3$, 4-Cl | 4-CH$_3$ |
| A-973 | 2-OCH$_3$, 5-Cl | 4-CH$_3$ |
| A-974 | 2-OCH$_3$, 6-Cl | 4-CH$_3$ |
| A-975 | 2-OCH$_3$, 5-OCH$_3$ | 4-CH$_3$ |
| A-976 | 2-OCH$_3$, 4-OCH$_3$ | 4-CH$_3$ |
| A-977 | 2-OCH$_3$, 3-OCH$_3$ | 4-CH$_3$ |
| A-978 | 2-OCH$_3$, 6-OCH$_3$ | 4-CH$_3$ |
| A-979 | 3-OCH$_3$, 5-OCH$_3$ | 4-CH$_3$ |
| A-980 | 3-OCH$_3$, 4-OCH$_3$ | 4-CH$_3$ |
| A-981 | — | 4-CF$_3$ |
| A-982 | 2-Cl | 4-CF$_3$ |
| A-983 | 2-F | 4-CF$_3$ |
| A-984 | 2-Br | 4-CF$_3$ |
| A-985 | 2-OCH$_3$ | 4-CF$_3$ |
| A-986 | 2-CF$_3$ | 4-CF$_3$ |
| A-987 | 2-C$_6$H$_5$ | 4-CF$_3$ |
| A-988 | 2-CH$_3$ | 4-CF$_3$ |
| A-989 | 3-Cl | 4-CF$_3$ |
| A-990 | 3-F | 4-CF$_3$ |
| A-991 | 3-Br | 4-CF$_3$ |
| A-992 | 3-OCH$_3$ | 4-CF$_3$ |
| A-993 | 3-CF$_3$ | 4-CF$_3$ |
| A-994 | 3-C$_6$H$_5$ | 4-CF$_3$ |
| A-995 | 3-CH$_3$ | 4-CF$_3$ |
| A-996 | 4-Cl | 4-CF$_3$ |
| A-997 | 4-F | 4-CF$_3$ |
| A-998 | 4-Br | 4-CF$_3$ |
| A-999 | 4-OCH$_3$ | 4-CF$_3$ |
| A-1000 | 4-CF$_3$ | 4-CF$_3$ |
| A-1001 | 4-C$_6$H$_5$ | 4-CF$_3$ |
| A-1002 | 4-CH$_3$ | 4-CF$_3$ |
| A-1003 | 2-Cl, 6-Cl | 4-CF$_3$ |
| A-1004 | 2-Cl, 5-Cl | 4-CF$_3$ |
| A-1005 | 2-Cl, 3-Cl | 4-CF$_3$ |
| A-1006 | 2-Cl, 4-Cl | 4-CF$_3$ |
| A-1007 | 3-Cl, 4-Cl | 4-CF$_3$ |
| A-1008 | 3-Cl, 5-Cl | 4-CF$_3$ |
| A-1009 | 2-F, 6-F | 4-CF$_3$ |
| A-1010 | 2-F, 5-F | 4-CF$_3$ |
| A-1011 | 2-F, 3-F | 4-CF$_3$ |
| A-1012 | 2-F, 4-F | 4-CF$_3$ |
| A-1013 | 3-F, 4-F | 4-CF$_3$ |
| A-1014 | 3-F, 5-F | 4-CF$_3$ |
| A-1015 | 2-F, 6-Cl | 4-CF$_3$ |
| A-1016 | 2-F, 5-Cl | 4-CF$_3$ |
| A-1017 | 2-F, 3-Cl | 4-CF$_3$ |
| A-1018 | 2-F, 4-Cl | 4-CF$_3$ |
| A-1019 | 3-F, 4-Cl | 4-CF$_3$ |
| A-1020 | 3-F, 5-Cl | 4-CF$_3$ |
| A-1021 | 2-Cl, 6-F | 4-CF$_3$ |
| A-1022 | 2-Cl, 5-F | 4-CF$_3$ |
| A-1023 | 2-Cl, 3-F | 4-CF$_3$ |
| A-1024 | 2-Cl, 4-F | 4-CF$_3$ |
| A-1025 | 3-Cl, 4-F | 4-CF$_3$ |
| A-1026 | 3-OCH$_3$, 4-Cl | 4-CF$_3$ |
| A-1027 | 3-OCH$_3$, 2-Cl | 4-CF$_3$ |
| A-1028 | 4-OCH$_3$, 3-Cl | 4-CF$_3$ |
| A-1029 | 4-OCH$_3$, 2-Cl | 4-CF$_3$ |
| A-1030 | 2-OCH$_3$, 3-Cl | 4-CF$_3$ |
| A-1031 | 2-OCH$_3$, 4-Cl | 4-CF$_3$ |
| A-1032 | 2-OCH$_3$, 5-Cl | 4-CF$_3$ |
| A-1033 | 2-OCH$_3$, 6-Cl | 4-CF$_3$ |
| A-1034 | 2-OCH$_3$, 5-OCH$_3$ | 4-CF$_3$ |
| A-1035 | 2-OCH$_3$, 4-OCH$_3$ | 4-CF$_3$ |
| A-1036 | 2-OCH$_3$, 3-OCH$_3$ | 4-CF$_3$ |
| A-1037 | 2-OCH$_3$, 6-OCH$_3$ | 4-CF$_3$ |
| A-1038 | 3-OCH$_3$, 5-OCH$_3$ | 4-CF$_3$ |
| A-1039 | 3-OCH$_3$, 4-OCH$_3$ | 4-CF$_3$ |
| A-1040 | — | 3-Cl, 4-Cl |
| A-1041 | 2-Cl | 3-Cl, 4-Cl |
| A-1042 | 2-F | 3-Cl, 4-Cl |
| A-1043 | 2-Br | 3-Cl, 4-Cl |
| A-1044 | 2-OCH$_3$ | 3-Cl, 4-Cl |
| A-1045 | 2-CF$_3$ | 3-Cl, 4-Cl |
| A-1046 | 2-C$_6$H$_5$ | 3-Cl, 4-Cl |
| A-1047 | 2-CH$_3$ | 3-Cl, 4-Cl |
| A-1048 | 3-Cl | 3-Cl, 4-Cl |
| A-1049 | 3-F | 3-Cl, 4-Cl |
| A-1050 | 3-Br | 3-Cl, 4-Cl |
| A-1051 | 3-OCH$_3$ | 3-Cl, 4-Cl |
| A-1052 | 3-CF$_3$ | 3-Cl, 4-Cl |
| A-1053 | 3-C$_6$H$_5$ | 3-Cl, 4-Cl |
| A-1054 | 3-CH$_3$ | 3-Cl, 4-Cl |
| A-1055 | 4-Cl | 3-Cl, 4-Cl |
| A-1056 | 4-F | 3-Cl, 4-Cl |
| A-1057 | 4-Br | 3-Cl, 4-Cl |
| A-1058 | 4-OCH$_3$ | 3-Cl, 4-Cl |
| A-1059 | 4-CF$_3$ | 3-Cl, 4-Cl |
| A-1060 | 4-C$_6$H$_5$ | 3-Cl, 4-Cl |
| A-1061 | 4-CH$_3$ | 3-Cl, 4-Cl |
| A-1062 | — | 3-OCH$_3$, 5-OCH$_3$ |
| A-1063 | 2-Cl | 3-OCH$_3$, 5-OCH$_3$ |
| A-1064 | 2-F | 3-OCH$_3$, 5-OCH$_3$ |
| A-1065 | 2-Br | 3-OCH$_3$, 5-OCH$_3$ |
| A-1066 | 2-OCH$_3$ | 3-OCH$_3$, 5-OCH$_3$ |
| A-1067 | 2-CF$_3$ | 3-OCH$_3$, 5-OCH$_3$ |
| A-1068 | 2-C$_6$H$_5$ | 3-OCH$_3$, 5-OCH$_3$ |
| A-1069 | 2-CH$_3$ | 3-OCH$_3$, 5-OCH$_3$ |
| A-1070 | 3-Cl | 3-OCH$_3$, 5-OCH$_3$ |
| A-1071 | 3-F | 3-OCH$_3$, 5-OCH$_3$ |
| A-1072 | 3-Br | 3-OCH$_3$, 5-OCH$_3$ |
| A-1073 | 3-OCH$_3$ | 3-OCH$_3$, 5-OCH$_3$ |
| A-1074 | 3-CF$_3$ | 3-OCH$_3$, 5-OCH$_3$ |
| A-1075 | 3-C$_6$H$_5$ | 3-OCH$_3$, 5-OCH$_3$ |
| A-1076 | 3-CH$_3$ | 3-OCH$_3$, 5-OCH$_3$ |
| A-1077 | 4-Cl | 3-OCH$_3$, 5-OCH$_3$ |
| A-1078 | 4-F | 3-OCH$_3$, 5-OCH$_3$ |
| A-1079 | 4-Br | 3-OCH$_3$, 5-OCH$_3$ |
| A-1080 | 4-OCH$_3$ | 3-OCH$_3$, 5-OCH$_3$ |
| A-1081 | 4-CF$_3$ | 3-OCH$_3$, 5-OCH$_3$ |
| A-1082 | 4-C$_6$H$_5$ | 3-OCH$_3$, 5-OCH$_3$ |
| A-1083 | 4-CH$_3$ | 3-OCH$_3$, 5-OCH$_3$ |
| A-1084 | — | 3-OCH$_3$, 4-Cl |
| A-1085 | 2-Cl | 3-OCH$_3$, 4-Cl |
| A-1086 | 2-F | 3-OCH$_3$, 4-Cl |
| A-1087 | 2-Br | 3-OCH$_3$, 4-Cl |
| A-1088 | 2-OCH$_3$ | 3-OCH$_3$, 4-Cl |
| A-1089 | 2-CF$_3$ | 3-OCH$_3$, 4-Cl |
| A-1090 | 2-C$_6$H$_5$ | 3-OCH$_3$, 4-Cl |
| A-1091 | 2-CH$_3$ | 3-OCH$_3$, 4-Cl |
| A-1092 | 3-Cl | 3-OCH$_3$, 4-Cl |
| A-1093 | 3-F | 3-OCH$_3$, 4-Cl |
| A-1094 | 3-Br | 3-OCH$_3$, 4-Cl |
| A-1095 | 3-OCH$_3$ | 3-OCH$_3$, 4-Cl |
| A-1096 | 3-CF$_3$ | 3-OCH$_3$, 4-Cl |
| A-1097 | 3-C$_6$H$_5$ | 3-OCH$_3$, 4-Cl |
| A-1098 | 3-CH$_3$ | 3-OCH$_3$, 4-Cl |
| A-1099 | 4-Cl | 3-OCH$_3$, 4-Cl |
| A-1100 | 4-F | 3-OCH$_3$, 4-Cl |
| A-1101 | 4-Br | 3-OCH$_3$, 4-Cl |
| A-1102 | 4-OCH$_3$ | 3-OCH$_3$, 4-Cl |

TABEL A-continued

| | (R¹)ₙ | (R²)ₘ |
|---|---|---|
| A-1103 | 4-CF₃ | 3-OCH₃, 4-Cl |
| A-1104 | 4-C₆H₅ | 3-OCH₃, 4-Cl |
| A-1105 | 4-CH₃ | 3-OCH₃, 4-Cl |
| A-1106 | — | 3-OCH₃, 2-Cl |
| A-1107 | 2-Cl | 3-OCH₃, 2-Cl |
| A-1108 | 2-F | 3-OCH₃, 2-Cl |
| A-1109 | 2-Br | 3-OCH₃, 2-Cl |
| A-1110 | 2-OCH₃ | 3-OCH₃, 2-Cl |
| A-1111 | 2-CF₃ | 3-OCH₃, 2-Cl |
| A-1112 | 2-C₆H₅ | 3-OCH₃, 2-Cl |
| A-1113 | 2-CH₃ | 3-OCH₃, 2-Cl |
| A-1114 | 3-Cl | 3-OCH₃, 2-Cl |
| A-1115 | 3-F | 3-OCH₃, 2-Cl |
| A-1116 | 3-Br | 3-OCH₃, 2-Cl |
| A-1117 | 3-OCH₃ | 3-OCH₃, 2-Cl |
| A-1118 | 3-CF₃ | 3-OCH₃, 2-Cl |
| A-1119 | 3-C₆H₅ | 3-OCH₃, 2-Cl |
| A-1120 | 3-CH₃ | 3-OCH₃, 2-Cl |
| A-1121 | 4-Cl | 3-OCH₃, 2-Cl |
| A-1122 | 4-F | 3-OCH₃, 2-Cl |
| A-1123 | 4-Br | 3-OCH₃, 2-Cl |
| A-1124 | 4-OCH₃ | 3-OCH₃, 2-Cl |
| A-1125 | 4-CF₃ | 3-OCH₃, 2-Cl |
| A-1126 | 4-C₆H₅ | 3-OCH₃, 2-Cl |
| A-1127 | 4-CH₃ | 3-OCH₃, 2-Cl |
| A-1128 | — | 4-OCH₃, 3-Cl |
| A-1129 | 2-Cl | 4-OCH₃, 3-Cl |
| A-1130 | 2-F | 4-OCH₃, 3-Cl |
| A-1131 | 2-Br | 4-OCH₃, 3-Cl |
| A-1132 | 2-OCH₃ | 4-OCH₃, 3-Cl |
| A-1133 | 2-CF₃ | 4-OCH₃, 3-Cl |
| A-1134 | 2-C₆H₅ | 4-OCH₃, 3-Cl |
| A-1135 | 2-CH₃ | 4-OCH₃, 3-Cl |
| A-1136 | 3-Cl | 4-OCH₃, 3-Cl |
| A-1137 | 3-F | 4-OCH₃, 3-Cl |
| A-1138 | 3-Br | 4-OCH₃, 3-Cl |
| A-1139 | 3-OCH₃ | 4-OCH₃, 3-Cl |
| A-1140 | 3-CF₃ | 4-OCH₃, 3-Cl |
| A-1141 | 3-C₆H₅ | 4-OCH₃, 3-Cl |
| A-1142 | 3-CH₃ | 4-OCH₃, 3-Cl |
| A-1143 | 4-Cl | 4-OCH₃, 3-Cl |
| A-1144 | 4-F | 4-OCH₃, 3-Cl |
| A-1145 | 4-Br | 4-OCH₃, 3-Cl |
| A-1146 | 4-OCH₃ | 4-OCH₃, 3-Cl |
| A-1147 | 4-CF₃ | 4-OCH₃, 3-Cl |
| A-1148 | 4-C₆H₅ | 4-OCH₃, 3-Cl |
| A-1149 | 4-CH₃ | 4-OCH₃, 3-Cl |
| A-1150 | — | 4-OCH₃, 2-Cl |
| A-1151 | 2-Cl | 4-OCH₃, 2-Cl |
| A-1152 | 2-F | 4-OCH₃, 2-Cl |
| A-1153 | 2-Br | 4-OCH₃, 2-Cl |
| A-1154 | 2-OCH₃ | 4-OCH₃, 2-Cl |
| A-1155 | 2-CF₃ | 4-OCH₃, 2-Cl |
| A-1156 | 2-C₆H₅ | 4-OCH₃, 2-Cl |
| A-1157 | 2-CH₃ | 4-OCH₃, 2-Cl |
| A-1158 | 3-Cl | 4-OCH₃, 2-Cl |
| A-1159 | 3-F | 4-OCH₃, 2-Cl |
| A-1160 | 3-Br | 4-OCH₃, 2-Cl |
| A-1161 | 3-OCH₃ | 4-OCH₃, 2-Cl |
| A-1162 | 3-CF₃ | 4-OCH₃, 2-Cl |
| A-1163 | 3-C₆H₅ | 4-OCH₃, 2-Cl |
| A-1164 | 3-CH₃ | 4-OCH₃, 2-Cl |
| A-1165 | 4-Cl | 4-OCH₃, 2-Cl |
| A-1166 | 4-F | 4-OCH₃, 2-Cl |
| A-1167 | 4-Br | 4-OCH₃, 2-Cl |
| A-1168 | 4-OCH₃ | 4-OCH₃, 2-Cl |
| A-1169 | 4-CF₃ | 4-OCH₃, 2-Cl |
| A-1170 | 4-C₆H₅ | 4-OCH₃, 2-Cl |
| A-1171 | 4-CH₃ | 4-OCH₃, 2-Cl |
| A-1172 | — | 2-OCH₃, 3-Cl |
| A-1173 | 2-Cl | 2-OCH₃, 3-Cl |
| A-1174 | 2-F | 2-OCH₃, 3-Cl |
| A-1175 | 2-Br | 2-OCH₃, 3-Cl |
| A-1176 | 2-OCH₃ | 2-OCH₃, 3-Cl |
| A-1177 | 2-CF₃ | 2-OCH₃, 3-Cl |
| A-1178 | 2-C₆H₅ | 2-OCH₃, 3-Cl |
| A-1179 | 2-CH₃ | 2-OCH₃, 3-Cl |
| A-1180 | 3-Cl | 2-OCH₃, 3-Cl |
| A-1181 | 3-F | 2-OCH₃, 3-Cl |
| A-1182 | 3-Br | 2-OCH₃, 3-Cl |
| A-1183 | 3-OCH₃ | 2-OCH₃, 3-Cl |
| A-1184 | 3-CF₃ | 2-OCH₃, 3-Cl |
| A-1185 | 3-C₆H₅ | 2-OCH₃, 3-Cl |
| A-1186 | 3-CH₃ | 2-OCH₃, 3-Cl |
| A-1187 | 4-Cl | 2-OCH₃, 3-Cl |
| A-1188 | 4-F | 2-OCH₃, 3-Cl |
| A-1189 | 4-Br | 2-OCH₃, 3-Cl |
| A-1190 | 4-OCH₃ | 2-OCH₃, 3-Cl |
| A-1191 | 4-CF₃ | 2-OCH₃, 3-Cl |
| A-1192 | 4-C₆H₅ | 2-OCH₃, 3-Cl |
| A-1193 | 4-CH₃ | 2-OCH₃, 3-Cl |
| A-1194 | — | 2-OCH₃, 4-Cl |
| A-1195 | 2-Cl | 2-OCH₃, 4-Cl |
| A-1196 | 2-F | 2-OCH₃, 4-Cl |
| A-1197 | 2-Br | 2-OCH₃, 4-Cl |
| A-1198 | 2-OCH₃ | 2-OCH₃, 4-Cl |
| A-1199 | 2-CF₃ | 2-OCH₃, 4-Cl |
| A-1200 | 2-C₆H₅ | 2-OCH₃, 4-Cl |
| A-1201 | 2-CH₃ | 2-OCH₃, 4-Cl |
| A-1202 | 3-Cl | 2-OCH₃, 4-Cl |
| A-1203 | 3-F | 2-OCH₃, 4-Cl |
| A-1204 | 3-Br | 2-OCH₃, 4-Cl |
| A-1205 | 3-OCH₃ | 2-OCH₃, 4-Cl |
| A-1206 | 3-CF₃ | 2-OCH₃, 4-Cl |
| A-1207 | 3-C₆H₅ | 2-OCH₃, 4-Cl |
| A-1208 | 3-CH₃ | 2-OCH₃, 4-Cl |
| A-1209 | 4-Cl | 2-OCH₃, 4-Cl |
| A-1210 | 4-F | 2-OCH₃, 4-Cl |
| A-1211 | 4-Br | 2-OCH₃, 4-Cl |
| A-1212 | 4-OCH₃ | 2-OCH₃, 4-Cl |
| A-1213 | 4-CF₃ | 2-OCH₃, 4-Cl |
| A-1214 | 4-C₆H₅ | 2-OCH₃, 4-Cl |
| A-1215 | 4-CH₃ | 2-OCH₃, 4-Cl |
| A-1216 | — | 2-OCH₃, 5-Cl |
| A-1217 | 2-Cl | 2-OCH₃, 5-Cl |
| A-1218 | 2-F | 2-OCH₃, 5-Cl |
| A-1219 | 2-Br | 2-OCH₃, 5-Cl |
| A-1220 | 2-OCH₃ | 2-OCH₃, 5-Cl |
| A-1221 | 2-CF₃ | 2-OCH₃, 5-Cl |
| A-1222 | 2-C₆H₅ | 2-OCH₃, 5-Cl |
| A-1223 | 2-CH₃ | 2-OCH₃, 5-Cl |
| A-1224 | 3-Cl | 2-OCH₃, 5-Cl |
| A-1225 | 3-F | 2-OCH₃, 5-Cl |
| A-1226 | 3-Br | 2-OCH₃, 5-Cl |
| A-1227 | 3-OCH₃ | 2-OCH₃, 5-Cl |
| A-1228 | 3-CF₃ | 2-OCH₃, 5-Cl |
| A-1229 | 3-C₆H₅ | 2-OCH₃, 5-Cl |
| A-1230 | 3-CH₃ | 2-OCH₃, 5-Cl |
| A-1231 | 4-Cl | 2-OCH₃, 5-Cl |
| A-1232 | 4-F | 2-OCH₃, 5-Cl |
| A-1233 | 4-Br | 2-OCH₃, 5-Cl |
| A-1234 | 4-OCH₃ | 2-OCH₃, 5-Cl |
| A-1235 | 4-CF₃ | 2-OCH₃, 5-Cl |
| A-1236 | 4-C₆H₅ | 2-OCH₃, 5-Cl |
| A-1237 | 4-CH₃ | 2-OCH₃, 5-Cl |
| A-1238 | — | 2-OCH₃, 6-Cl |
| A-1239 | 2-Cl | 2-OCH₃, 6-Cl |
| A-1240 | 2-F | 2-OCH₃, 6-Cl |
| A-1241 | 2-Br | 2-OCH₃, 6-Cl |
| A-1242 | 2-OCH₃ | 2-OCH₃, 6-Cl |
| A-1243 | 2-CF₃ | 2-OCH₃, 6-Cl |
| A-1244 | 2-C₆H₅ | 2-OCH₃, 6-Cl |
| A-1245 | 2-CH₃ | 2-OCH₃, 6-Cl |
| A-1246 | 3-Cl | 2-OCH₃, 6-Cl |
| A-1247 | 3-F | 2-OCH₃, 6-Cl |
| A-1248 | 3-Br | 2-OCH₃, 6-Cl |
| A-1249 | 3-OCH₃ | 2-OCH₃, 6-Cl |
| A-1250 | 3-CF₃ | 2-OCH₃, 6-Cl |
| A-1251 | 3-C₆H₅ | 2-OCH₃, 6-Cl |
| A-1252 | 3-CH₃ | 2-OCH₃, 6-Cl |
| A-1253 | 4-Cl | 2-OCH₃, 6-Cl |
| A-1254 | 4-F | 2-OCH₃, 6-Cl |
| A-1255 | 4-Br | 2-OCH₃, 6-Cl |
| A-1256 | 4-OCH₃ | 2-OCH₃, 6-Cl |

TABEL A-continued

| | $(R^1)_n$ | $(R^2)_m$ |
|---|---|---|
| A-1257 | 4-CF$_3$ | 2-OCH$_3$, 6-Cl |
| A-1258 | 4-C$_6$H$_5$ | 2-OCH$_3$, 6-Cl |
| A-1259 | 4-CH$_3$ | 2-OCH$_3$, 6-Cl |
| A-1260 | — | 2-Cl, 5-Cl |
| A-1261 | 2-Cl | 2-Cl, 5-Cl |
| A-1262 | 2-F | 2-Cl, 5-Cl |
| A-1263 | 2-Br | 2-Cl, 5-Cl |
| A-1264 | 2-OCH$_3$ | 2-Cl, 5-Cl |
| A-1265 | 2-CF$_3$ | 2-Cl, 5-Cl |
| A-1266 | 2-C$_6$H$_5$ | 2-Cl, 5-Cl |
| A-1267 | 2-CH$_3$ | 2-Cl, 5-Cl |
| A-1268 | 3-Cl | 2-Cl, 5-Cl |
| A-1269 | 3-F | 2-Cl, 5-Cl |
| A-1270 | 3-Br | 2-Cl, 5-Cl |
| A-1271 | 3-OCH$_3$ | 2-Cl, 5-Cl |
| A-1272 | 3-CF$_3$ | 2-Cl, 5-Cl |
| A-1273 | 3-C$_6$H$_5$ | 2-Cl, 5-Cl |
| A-1274 | 3-CH$_3$ | 2-Cl, 5-Cl |
| A-1275 | 4-Cl | 2-Cl, 5-Cl |
| A-1276 | 4-F | 2-Cl, 5-Cl |
| A-1277 | 4-Br | 2-Cl, 5-Cl |
| A-1278 | 4-OCH$_3$ | 2-Cl, 5-Cl |
| A-1279 | 4-CF$_3$ | 2-Cl, 5-Cl |
| A-1280 | 4-C$_6$H$_5$ | 2-Cl, 5-Cl |
| A-1281 | 4-CH$_3$ | 2-Cl, 5-Cl |
| A-1282 | — | 2-Cl, 4-Cl |
| A-1283 | 2-Cl | 2-Cl, 4-Cl |
| A-1284 | 2-F | 2-Cl, 4-Cl |
| A-1285 | 2-Br | 2-Cl, 4-Cl |
| A-1286 | 2-OCH$_3$ | 2-Cl, 4-Cl |
| A-1287 | 2-CF$_3$ | 2-Cl, 4-Cl |
| A-1288 | 2-C$_6$H$_5$ | 2-Cl, 4-Cl |
| A-1289 | 2-CH$_3$ | 2-Cl, 4-Cl |
| A-1290 | 3-Cl | 2-Cl, 4-Cl |
| A-1291 | 3-F | 2-Cl, 4-Cl |
| A-1292 | 3-Br | 2-Cl, 4-Cl |
| A-1293 | 3-OCH$_3$ | 2-Cl, 4-Cl |
| A-1294 | 3-CF$_3$ | 2-Cl, 4-Cl |
| A-1295 | 3-C$_6$H$_5$ | 2-Cl, 4-Cl |
| A-1296 | 3-CH$_3$ | 2-Cl, 4-Cl |
| A-1297 | 4-Cl | 2-Cl, 4-Cl |
| A-1298 | 4-F | 2-Cl, 4-Cl |
| A-1299 | 4-Br | 2-Cl, 4-Cl |
| A-1300 | 4-OCH$_3$ | 2-Cl, 4-Cl |
| A-1301 | 4-CF$_3$ | 2-Cl, 4-Cl |
| A-1302 | 4-C$_6$H$_5$ | 2-Cl, 4-Cl |
| A-1303 | 4-CH$_3$ | 2-Cl, 4-Cl |
| A-1304 | — | 2-Cl, 3-Cl |
| A-1305 | 2-Cl | 2-Cl, 3-Cl |
| A-1306 | 2-F | 2-Cl, 3-Cl |
| A-1307 | 2-Br | 2-Cl, 3-Cl |
| A-1308 | 2-OCH$_3$ | 2-Cl, 3-Cl |
| A-1309 | 2-CF$_3$ | 2-Cl, 3-Cl |
| A-1310 | 2-C$_6$H$_5$ | 2-Cl, 3-Cl |
| A-1311 | 2-CH$_3$ | 2-Cl, 3-Cl |
| A-1312 | 3-Cl | 2-Cl, 3-Cl |
| A-1313 | 3-F | 2-Cl, 3-Cl |
| A-1314 | 3-Br | 2-Cl, 3-Cl |
| A-1315 | 3-OCH$_3$ | 2-Cl, 3-Cl |
| A-1316 | 3-CF$_3$ | 2-Cl, 3-Cl |
| A-1317 | 3-C$_6$H$_5$ | 2-Cl, 3-Cl |
| A-1318 | 3-CH$_3$ | 2-Cl, 3-Cl |
| A-1319 | 4-Cl | 2-Cl, 3-Cl |
| A-1320 | 4-F | 2-Cl, 3-Cl |
| A-1321 | 4-Br | 2-Cl, 3-Cl |
| A-1322 | 4-OCH$_3$ | 2-Cl, 3-Cl |
| A-1323 | 4-CF$_3$ | 2-Cl, 3-Cl |
| A-1324 | 4-C$_6$H$_5$ | 2-Cl, 3-Cl |
| A-1325 | 4-CH$_3$ | 2-Cl, 3-Cl |
| A-1326 | — | 2-Cl, 6-Cl |
| A-1327 | 2-Cl | 2-Cl, 6-Cl |
| A-1328 | 2-F | 2-Cl, 6-Cl |
| A-1329 | 2-Br | 2-Cl, 6-Cl |
| A-1330 | 2-OCH$_3$ | 2-Cl, 6-Cl |
| A-1331 | 2-CF$_3$ | 2-Cl, 6-Cl |
| A-1332 | 2-C$_6$H$_5$ | 2-Cl, 6-Cl |
| A-1333 | 2-CH$_3$ | 2-Cl, 6-Cl |

TABEL A-continued

| | $(R^1)_n$ | $(R^2)_m$ |
|---|---|---|
| A-1334 | 3-Cl | 2-Cl, 6-Cl |
| A-1335 | 3-F | 2-Cl, 6-Cl |
| A-1336 | 3-Br | 2-Cl, 6-Cl |
| A-1337 | 3-OCH$_3$ | 2-Cl, 6-Cl |
| A-1338 | 3-CF$_3$ | 2-Cl, 6-Cl |
| A-1339 | 3-C$_6$H$_5$ | 2-Cl, 6-Cl |
| A-1340 | 3-CH$_3$ | 2-Cl, 6-Cl |
| A-1341 | 4-Cl | 2-Cl, 6-Cl |
| A-1342 | 4-F | 2-Cl, 6-Cl |
| A-1343 | 4-Br | 2-Cl, 6-Cl |
| A-1344 | 4-OCH$_3$ | 2-Cl, 6-Cl |
| A-1345 | 4-CF$_3$ | 2-Cl, 6-Cl |
| A-1346 | 4-C$_6$H$_5$ | 2-Cl, 6-Cl |
| A-1347 | 4-CH$_3$ | 2-Cl, 6-Cl |

Amongst compounds of the formula I, preference is given to the following compounds of the formula I-B, wherein A in formula I is a radical A$^2$ with X being S, and wherein the variables n, m, R$^1$ and R$^2$ have the meanings given above.

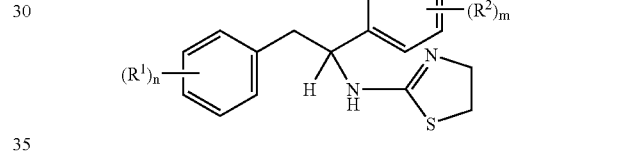

(I-B)

Examples of these compounds are those wherein (R$^1$)$_n$ and (R$^2$)$_m$ have the meanings given in each line of table A (Compounds I-B.1 to I-B.1347).

Amongst compounds of the formula I, preference is also given to the following compounds of the formula I-C, wherein A in formula I is a radical A$^1$ with X being O and R$^6$ being CH$_3$, and wherein the variables n, m, R$^1$ and R$^2$ have the meanings given above.

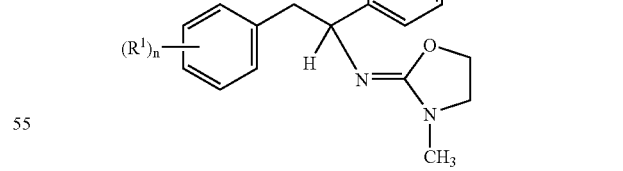

(I-C)

Examples of these compounds are those wherein (R$^1$)$_n$ and (R$^2$)$_m$ have the meanings given in each line of table A (Compounds I-C.1 to I-C.1347).

Amongst compounds of the formula I, preference is also given to the following compounds of the formula I-D, wherein A in formula I is a radical A$^1$ with X being S and R$^6$ being CH$_3$, and wherein the variables n, m, R$^1$ and R$^2$ have the meanings given above.

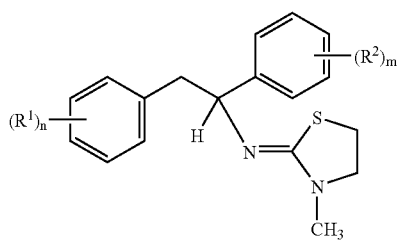
(I-D)

Examples of these compounds are those wherein $(R^1)_n$ and $(R^2)_m$ have the meanings given in each line of table A (Compounds I-D.1 to I-D.1347).

Amongst compounds of the formula I, preference is also given to the following compounds of the following formulae I-E, I-F, I-G, I-H, I-J, I-K, I-L and I-M, wherein the variables n, m, $R^1$ and $R^2$ have the meanings given above.

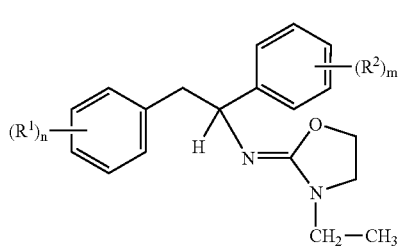
(I-E)

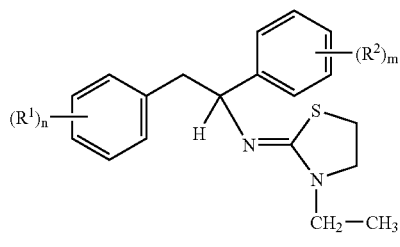
(I-F)

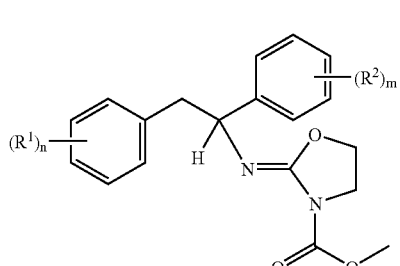
(I-G)

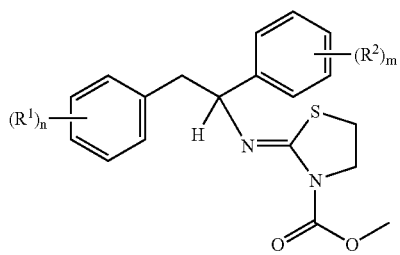
(I-H)

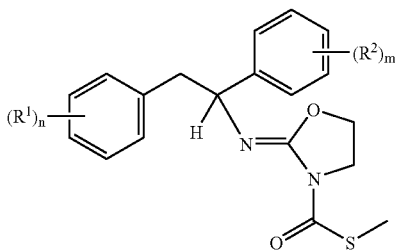
(I-J)

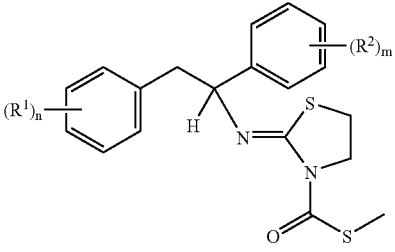
(I-K)

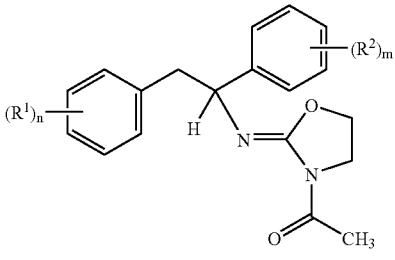
(I-L)

(I-M)

Examples of these compounds are those wherein $(R^1)_n$ and $(R^2)_m$ have the meanings given in each line of table A (Compounds I-E.1 to I-E.1347, I-F.1 to I-F.1347, I-G.1 to IG.1347, I-H.1 to I-H.1347, I-J.1 to I-J.1347, I-K.1 to I-K.1347, I-L.1 to I-L.1347 and I-M.1 to I-M.1347).

The compounds of the present invention can be e.g. prepared from the corresponding diphenylethylamines II by the synthetic routes outlined in schemes 1 and 2. Compounds of the formula I, wherein A is a radical $A^2$ with X being S and $R^7$ being H can be obtained according to the method outlined in scheme 1:

Scheme 1:

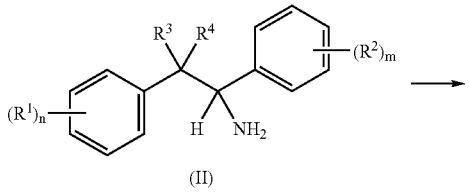
(II)

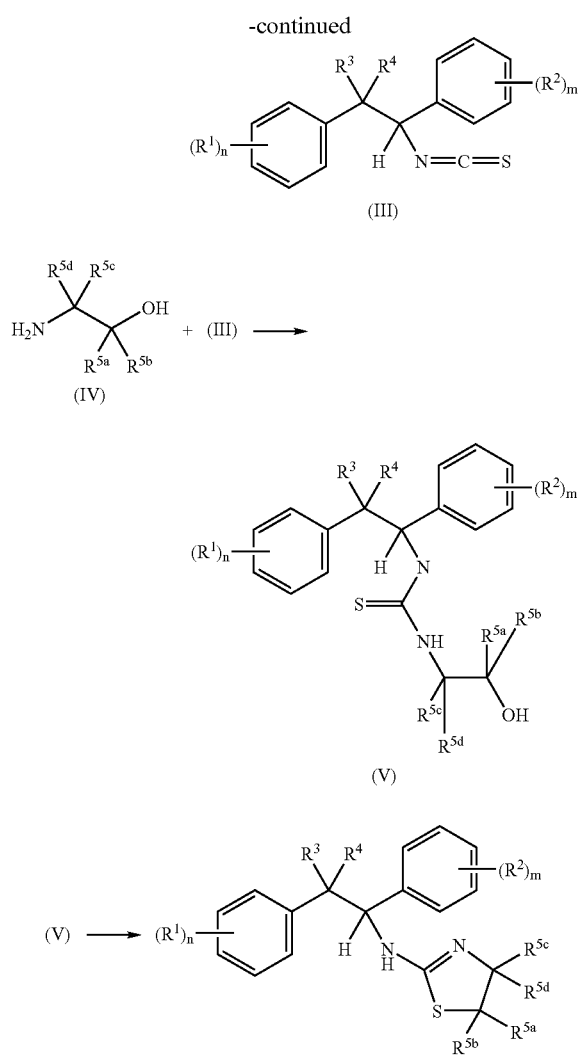

According to the method outlined in scheme 1, a 1,2-diphenylaminoethane II is converted into the corresponding isothiocyanate III by conventional means, e.g. by reacting II with thiophosgene (see e.g. Houben-Weyl, E4, "Methoden der Organischen Chemie", chapter IIIc, pp. 837-842. The isothiocyanate III is then reacted with an aminoethanol of the general formula IV, thereby obtaining the thiourea compound of the formula V. The reaction of the aminoethanol IV with isothiocyanate III can be performed in accordance with standard methods of organic chemistry, see e.g. Biosci. Biotech. Biochem. 1992, 56 (7), 1062-1065.

The thus obtained thioureas can be cyclized by conventional means thereby obtaining the desired thiazoline compound of the formula I, wherein A is $A^2$ with X being S and $R^7$ being H. Cyclization of compound V can be achieved e.g. under acid catalysis or under dehydrating conditions e.g. by Mitsunobu's reaction (see Tetrahedron Letters 1999, 40, 3125-3128).

Compounds of the formula I, wherein A is a radical $A^2$ with X being O and $R^7$ being H can be obtained by a route similar to the method outlined in scheme 1 (see also Pestic. Biochem. Physiol. 1988, 30, 190-197). Unlike the method of scheme I diphenylaminoethane II is converted into the corresponding isocyanate IIIa, e.g. by reaction with phosgen, diphosgen or another phosgene equivalent. The isocyante IIIa is then reacted with aminoethanol IV and the thus obtained urea is cyclized.

Compounds of the formula I, wherein A is a radical of the formula $A^2$ with X being O and $R^7$ being H can also be obtained by the method outlined in scheme 2. In scheme 2 the variable Hal is halogen, especially chlorine. Y is OH or halogen. Z is hydrogen, alkyl or halogen, especially fluorine.

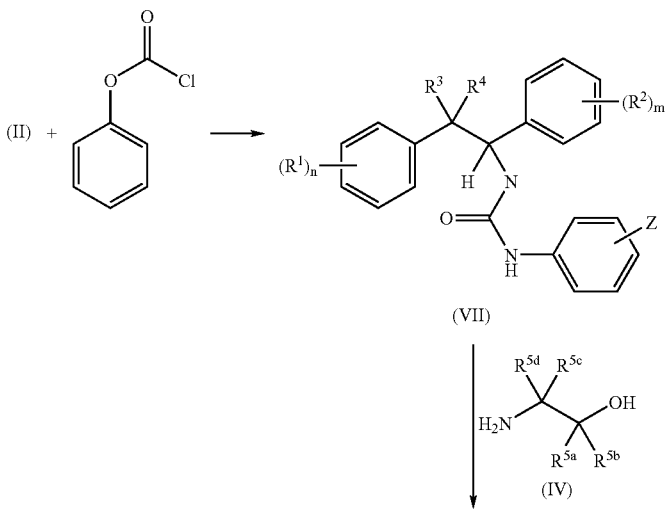

-continued

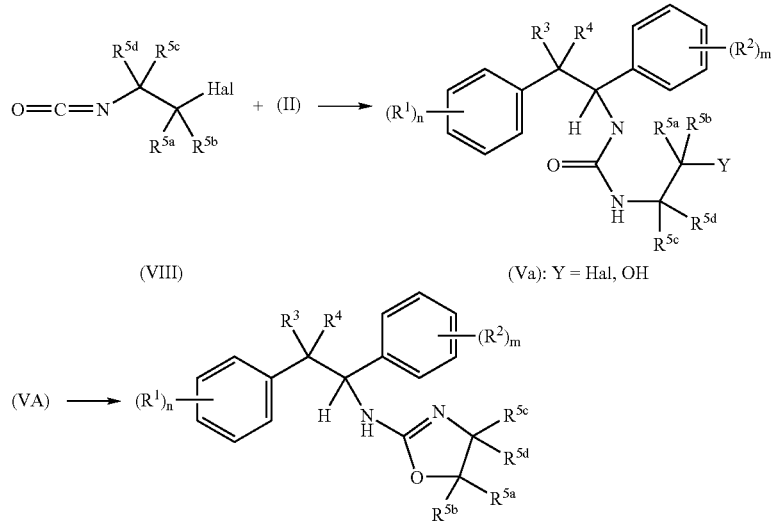

(VIII)    (Va): Y = Hal, OH (VA) →

According to scheme 2, diphenylaminoethanes are converted into the corresponding carbamates of the formula VII by reacting II with a phenyl chloroformate such as 4-chlorophenyl chloroformat according to standard methods (see e.g. Pesticide Biochemistry and Physiology 30, 1988, p. 190-197). The thus obtained carbamate VII is reacted with the aminoalkohol IV in the presence of trimethylchlorosilane according to the method described in J. Org. Chem. 1998, 63, 8515-8521. Thereby, 2-hydroxyethyl ureas of the formula Va {Y=OH} are obtained. The 2-hydroxyethylureas can be cyclized to the oxazoline compounds I according to the procedures described in Org. Lett. 1999, 1, 1705-1708 or Tetrahedron Lett. 1992, 33, 2807-2810.

Alternatively, substituted 2-chloroethyl ureas Va{X=Cl} can be cyclized according to the methods described in Bioorg. Med. Chem. Lett. 1994, 4, 2317-2322 or under the conditions described below. Chloroethyl ureas Va can be obtained from the corresponding diphenylethylamines II by reacting II with 2-Chloroethylisocyanate VIII.

Compounds of formula I, wherein A in formula I is a radical $A^1$ with $R^6$ being different from hydrogen or a Radical $A^2$ with $R^7$ different from hydrogen, can be obtained from compounds of the formula I with $R^6$ (or $R^7$, respectively) as a starting material.

In order to obtain compounds of the formula I, wherein $R^6$ or $R^7$ is $C_1$-$C_6$-alkyl or alkyl $C_1$-$C_6$-alkylcarbonyl, the starting material is reacted with a suitable alkylating or acylating agent $R^a$-L, wherein L is a leaving group, e.g. halogen and $R^a$ is $C_1$-$C_6$-alkyl or alkyl $C_1$-$C_6$-alkylcarbonyl. The reaction can be performed by routine methods described in standard textbooks on organic synthesis, see e.g. J. March, Advanced Organic Synthesis, $3^{rd}$ ed. John Wiley and Sons.

In order to obtain compounds of the formula I, wherein $R^6$ or $R^7$ is $C_1$-$C_6$-alkyloxycarbonyl or $C_1$-$C_6$-alkylthiocarbonyl, the starting material is reacted with a suitable haloformiate of the formula $R^b$—C(O)-Hal, wherein Hal is halogen, especially chlorine and wherein $R^b$ is $C_1$-$C_6$-alkyloxy or $C_1$-$C_6$-alkylthio. The reaction can be performed by routine methods described in standard textbooks on organic synthesis, see e.g. J. March, Advanced Organic Synthesis, $3^{rd}$ ed. John Wiley and Sons.

The cyano group can be introduced as a radical $R^6$ or $R^7$ e.g. by reaction of the starting material with bromocyan according to the methods described in the experimental part of the present application. The introduction of nitro groups as radicals $R^6$ or $R^7$ can be performed by reacting compounds I with $R^6$ or $R^7$ being H with nitronium source according to standard methods well known in the art.

The group $(SO_2)NR^aR^b$ can be introduced as a radical $R^6$ or $R^7$ e.g. by reacting the starting material with the chlorosulfonamide Cl—$(SO_2)NR^aR^b$ according to routine methods described in standard textbooks on organic synthesis, see e.g. J. March, Advanced Organic Synthesis, $3^{rd}$ ed. John Wiley and Sons.

The group $C(O)NR^aR^b$ can be introduced as a radical $R^6$ or $R^7$ e.g. by reacting the starting material with the chloroformamide Cl—CO—$NR^aR^b$ or by reaction with isocyanates OCN—$R^a$ for $R^b$ being hydrogen.

Diphenylethylamines of the formula II are known in the art (e.g. 1,2-diphenylethylamine, CAS-Nr.[3082-58-4]) or they can be prepared by methods familiar to an Organic chemist and well known in the art. Suitable methods for preparing Diphenylethylamines II comprise inter alia the reductive amination of the corresponding phenylbenzylketones or the reduction of the corresponding phenylbenzyloximes (see e.g. J. Med. Chem. 1995, 38, 1600-1607; J. Med. Chem 1994, 37 (7), 913-923). Diphenylethylamines of the formula II can be also prepared by the addition of phenyl- or benzyl-organometallic reagents to a suitable imines such as a tert.-butylsulfinylimine of a benzaldehyd- or 2-phenylethanal compound according to the method described in Tetrahedron, 1999, 55, S. 8883-8904.

2-Aminoethanol-compounds IV and 2-aminoethylisocyanates VIII are commercially available or they can be prepared according to routine methods, which are familiar to an Organic chemist.

Due to their excellent activity, the compounds of the general formula I may be used for controlling animal pests, selected harmful insects, arachnids and nematodes. Accordingly, the invention further provides agriculturally composition for combating such animal pests, which comprises such an amount of at least one compound of the general formula I or at least an agriculturally useful salt of I and at least one inert liquid and/or solid agronomically acceptable carrier that it has a pesticidal action and, if desired, at least one surfactant.

Such a composition may contain a single active compound of the general formula I or a mixture of several active compounds I according to the present invention. The composition according to the present invention may comprise an individual isomer or mixtures of isomers as well as individual tautomers or mixtures of tautomers.

The compounds of the formula I and the pesticidal compositions comprising them are effective agents for controlling animal pests, selected from insects, arachnids and nematodes. Animal pests controlled by the compounds of formula I include for example:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byotiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicomis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria;* dipterans (*Diptera*), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (*Thysanoptera*), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (*Hymenoptera*), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (*Heteroptera*), e.g. *Acrostemum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtli, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus homi, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand,* and *Viteus vitifolii;* termites (*Isoptera*), e.g. *Calotermes flavicollis, Leucotermes flavipes, Reticulitermes flavipes, Reticulitermes lucifugus und Termes natalensis;* orthopterans (*Orthoptera*), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;*

Arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum,*

*Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendaii, Phyllocoptrata oleivora* and *Eriophyes sheldoni, Tarsonemidae* spp. such as *Phytonemus pallidus* and *Polyphagotarsonemus latus; Tenuipalpidae* spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;*

Siphonatera, e.g. *Xenopsylla cheopsis, Ceratophyllus* spp;

Nematodes, including plant parasitic nematodes and nematodes living in the soil.

Plant parasitic nematodes include, such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formula I are used for controlling insects or arachnids, in particular insects of the orders Lepidoptera, Coleoptera and Homoptera and arachnids of the order Acarina. The compounds of the formula I according to the present invention are particularly useful for controlling insects of the order Lepidoptera and Homoptera.

The compounds of formula (I) or the pesticidal compositions comprising them may be used to protect growing plants and crops from attack or infestation by animal pests, especially insects, acaridae or arachnids by contacting the plant/crop with a pesticidally effective amount of compounds of formula (I). The term "crop" refers both to growing and harvested crops.

The animal pest, i.e. the insects, arachnids, and nematodes, the plant, soil or water in which the plant is growing can be contacted with the present compound(s) I or composition(s) containing them by any application method known in the art.

As such, "contacting" includes both direct contact (applying the compounds/compositions directly on the animal pest or plant—typically to the foliage, stem or roots of the plant) and indirect contact (applying the compounds/compositions to the locus of the animal pest or plant).

Moreover, animal pests may be controlled by contacting the target pest, its food supply or its locus with a pesticidally effective amount of compounds of formula (I). As such, the application may be carried out before or after the infection of the locus, growing crops, or harvested crops by the pest.

"Locus" means a habitat, breeding ground, plant, seed, soil, area, material or environment in which a pest or parasite is growing or may grow.

Effective amounts suitable for use in the method of invention may vary depending upon the particular formula I compound, target pest, method of application, application timing, weather conditions, animal pest habitat, or the like. In general, for use in treating crop plants, the rate of application of the compounds I and/or compositions according to this invention may be in the range of about 0.1 g to about 4000 g per hectare, desirably from about 25 g to about 600 g per hectare, more desirably from about 50 g to about 500 g per hectare. For use in treating seeds, the typical rate of application is of from about 1 g to about 500 g per kilogram of seeds, desirably from about 2 g to about 300 g per kilogram of seeds, more desirably from about 10 g to about 200 g per kilogram of seeds. Customary application rates in the protection of materials are, for example, from about 0.001 g to about 2000 g, desirably from about 0.005 g to about 1000 g, of active compound per cubic meter of treated material.

The compounds I or the pesticidal compositions comprising them can be used, for example in the form of solutions, emulsions, microemulsions, suspensions, flowable concentrates, dusts, powders, pastes and granules. The use form depends on the particular purpose; in any case, it should guarantee a fine and uniform distribution of the compound according to the invention.

The pesticidal composition for combating animal pests, i.e. insects, arachnids, or nematodes, contains such an amount of at least one compound of the general formula I or an agriculturally useful salt of I and auxiliaries which are usually used in formulating pesticidal composition.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly-disperse silica, silicates); emulsifiers such as non-ionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutyinaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, compacted granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

Such formulations or compositions of the present invention include a formula I compound of this invention (or combinations thereof) admixed with one or more agronomically acceptable inert, solid or liquid carriers. Those compositions contain a pesticidally effective amount of said compound or compounds, which amount may vary depending upon the particular compound, target pest, and method of use.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-$\alpha$-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-$\alpha$-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Compositions to be used according to this invention may also contain other active ingredients, for example other pesticides, insecticides, herbicides, fungicides, other pesticides, or bactericides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds I or the compositions comprising them in the use form as pesticides with other pesticides frequently results in a broader pesticidal spectrum of action.

The following list of pesticides together with which the compounds of formula I can be used, is intended to illustrate the possible combinations, but not to impose any limitation:

Organophosphates: Acephate, Azinphos-methyl, Chlorpyrifos, Chlorfenvinphos, Diazinon, Dichlorvos, Dicrotophos, Dimethoate, Disulfoton, Ethion, Fenitrothion, Fenthion, Isoxathion, Malathion, Methamidophos, Methidathion, Methyl-Parathion, Mevinphos, Monocrotophos, Oxydemeton-methyl, Paraoxon, Parathion, Phenthoate, Phosalone, Phosmet, Phosphamidon, Phorate, Phoxim, Pirimiphos-methyl, Profenofos, Prothiofos, Sulprophos, Triazophos, Trichlorfon;

Carbamates: Alanycarb, Benfuracarb, Carbaryl, Carbosulfan, Fenoxycarb, Furathiocarb, Indoxacarb, Methiocarb, Methomyl, Oxamyl, Pirimicarb, Propoxur, Thiodicarb, Triazamate;

Pyrethroids: Bifenthrin, Cyfluthrin, Cypermethrin, Deltamethrin, Esfenvalerate, Ethofenprox, Fenpropathrin, Fenvalerate, Cyhalothrin, Lambda-Cyhalothrin, Permethrin, Silafluofen, Tau-Fluvalinate, Tefluthrin, Tralomethrin, Zeta-Cypermethrin;

Arthropod growth regulators: a) chitin synthesis inhibitors: benzoylureas: Chlorfluazuron, Diflubenzuron, Flucycloxuron, Flufenoxuron, Hexaflumuron, Lufenuron, Novaluron, Teflubenzuron, Triflumuron; Buprofezin, Diofenolan, Hexythiazox, Etoxazole, Clofentazine; b) ecdysone antagonists: Halofenozide, Methoxyfenozide, Tebufenozide; c) juvenoids: Pyriproxyfen, Methoprene, Fenoxycarb; d) lipid biosynthesis inhibitors: Spirodiclofen;

Various: Abamectin, Acequinocyl, Amitraz, Azadirachtin, Bifenazate, Cartap, Chlorfenapyr, Chlordimeform, Cyromazine, Diafenthiuron, Dinetofuran, Diofenolan, Emamectin, Endosulfan, Ethiprole, Fenazaquin, Fipronil, Formetanate, Formetanate hydrochloride, Hydramethylnon, Imidacloprid, lndoxacarb, Pyridaben, Pymetrozine, Spinosad, Sulfur, Tebufenpyrad, Thiamethoxam, and Thiocyclam.

The present invention is now illustrated in further detail by the following examples.

The compounds of the invention as well as intermediates were characterized by coupled High Performance Liquid Chromatography/mass spectroscopy (HPLC/MS), by NMR or by their melting points. HPLC column: RP-18 column (Chromolith Speed ROD from Merck KgaA, Germany). Elution: acetonitrile+0.1% trifluoroacetic acid (TFA)/water+ 0.1% TFA in a ratio of from 5:95 to 95:5 in 5 minutes at 40° C. MS Quadrupol electrospray ionisation, 80 V (positive modus).

EXAMPLE 1

(4,5-Dihydro-4-methyloxazol-2-yl)-[2-(3-chlorophenyl)-1-phenyl-ethyl]-amine 1.1 1-(2-(3-Chlorophenyl)-1-phenyl-ethyl)-3-(2-chloro-propyl)-urea 72 mg (0.6 mmol) 2-chloropropyl isocyanate in THF were added in 4 portions to 116 mg (0.5 mmol) 2-(3-chlorophenyl)-1-phenyl-ethyl amine in 2 ml THF at 0° C. over a time of 4 hours. The solution was stirred at room temperature overnight. After evaporation of the solvent and aqueous work-up 128 mg (0.36 mmol, 73%) of the desired urea were obtained.

1.2 (4,5-Dihydro-4-methyloxazol-2-yl)-[2-(3-chlorophenyl)-1-phenyl-ethyl]-amine 158 mg (0.45 mmol) 1-(2-(3-Chlorophenyl)-1-phenyl-ethyl)-3-(2-chloro-propyl)-urea and 386 mg (0.9 mmol) 1,5,7-triazabicyclo[4.4.0]dec-5-ene-7-methyl polystyrene (TBD-methyl polystyrene, Novabiochem) were heated to 100° C. in 1,4-dioxane for 12 h. After removal of the polymer by filtration and evaporation of the solvent 92 mg (0.31 mmol, 69%) of the desired amino oxazoline were obtained.

EXAMPLE 2

(4,5-Dihydro-oxazol-2-yl)-[2-(4-fluoro-phenyl)-1-phenyl-ethyl]-amine

A solution of 2-(4-fluoro-phenyl)-1-phenyl-ethylamine (1.50 g) in THF was treated dropwise with 2-chloroethyl isocyanate (0.89 g) at 0° C. After stirring overnight at room temperature the solvent was evaporated and the residue dissolved in dimethoxy ethane (25 ml). DBU (1,8-diazabicyclo[5.4.0]undec-7-en) was added (1.78 g) and the reaction mixture heated under reflux for 1 hour. Column chromatography on silica yielded 1.3 g of the title compound.

EXAMPLE 3

1-[1-(4-Chlorophenyl)-2-phenyl-ethyl]-(4,5-dihydrothiazol-2-yl)-amine 3.1 1-(4-Chlorophenyl)-2-phenyl-ethylamine An autoclave (300 ml, hasteloi) was charged with 1-(4-chlorophenyl)-2-phenylethanone (22 g), tetrahydrofurane (90 ml), cobalt activated Raney-nickel (5 g) and ammonia (45 g). The autoclave was flushed with nitrogen and heated to 70° C. Hydrogen was added at this temperature up to a pressure of 150 bar, the reaction temperature increased to 110° C. After stirring overnight the reaction mixture was filtered through silica and washed with THF. Aqueous work-up with extraction into dichloro methane yielded pure amine in 83% yield.

3.2 1-Chloro-4-(1-isothiocyanato-1-phenylethan-2-yl)benzene 1-(4-Chlorophenyl)-2-phenylethylamine (4.86 g) was added to a mixture of thiophosgen (2.88 g) in dichloromethane (40 ml), potassium carbonate (8.56 g) and water (10 ml). The mixture was stirred overnight. Then, the reaction mixture was poured into water and the aqueous phase was extracted with dichloromethane to yield 5.67 g (99%) of the isothiocyante compound.

3.3 1-[1-(4-Chlorophenyl)-2-phenylethyl]-3-(2-hydroxyethyl)-thiourea

A solution of 1-chloro-4-(1-isothiocyanato-2-phenylethyl) benzene (0.50 g) in chloroform (30 ml) was treated with ethanolamine (0.11 g) and stirred overnight at room temperature. Chromatography on silica yielded the product (0.30 g)

3.4 1-[1-(4-Chlorophenyl)-2-phenyl-ethyl]-(4,5-dihydrothiazol-2-yl)-amine

1-[1-(4-Chlorophenyl)-2-phenyl-ethyl]-3-(2-hydroxyethyl)-thiourea (0.30 g) was refluxed with concentrated hydrochloric acid and stirring was continued at room temperature overnight. The hydrochloric acid phase was removed from the resulting oil by decantation. The residue was dissolved in ethyl acetate and the organic phase was washed with aqueous potassium carbonate solution and water. After drying and evaporating the solvent 0.14 g of 1-[1-(4-Chlorophenyl)-2-phenyl-ethyl]-(4,5-dihydrothiazol-2-yl)-amine were obtained.

The compounds of the general formula Ia (examples 4 to 44) can be prepared accordingly. The spectroscopical data of these compounds are listed in table 1.

TABLE 1

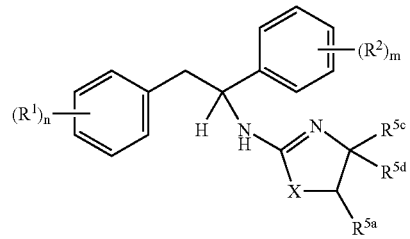

(Ia)

| Ex. | $(R^1)_n$ | $(R^2)_m$ | $R^{5a}$ | $R^{5c}$ | $R^{5d}$ | X | Physico-chemical data (m.p. [° C.]; $^1$H-NMR (CDCl$_3$): δ [ppm]; HPLC-MS: RT [min], molecular mass |
|---|---|---|---|---|---|---|---|
| 1 | 3-Cl | — | H | CH$_3$ | H | O | 2.861<br>315 [M + H]$^+$ |
| 2 | 4-F | — | H | H | H | O | 141-143° C. |
| 3 | — | 4-Cl | H | H | H | S | 3.05 (mc), 3.25 (t), 3.85 (t), 4.90 (mc), 7.0-7.3 (m) |
| 4 | — | — | H | H | H | O | 2.585<br>267 [M + H]$^+$ |
| 5 | 3-Cl | — | H | H | H | S | 2.9 (mc0, 3.1 (mc), 3.65 (mc), 4.9 (mc), 7.1-7.4 (m) |
| 6 | — | — | H | H | H | S | 114-116° C. |
| 7 | 3-CH$_3$ | — | H | H | H | S | 2.25 (s), 3.0 (mc), 3.5-4.9 (m), 5.1 (mc), 7.0-7.5 (m) |
| 8 | 3-Cl | — | H | n-Butyl | H | S | 0.7-0.9 (M), 1-0-1.4 (m), 2.7-3.3 (m), 3.9 (mc), 4.9 (mc), 7.1-7.4 (m) |
| 9 | 3-Cl | — | H | Benzyl | H | S | 2.4-3.1 (m), 4.2 (mc), 4.9 (mc), 6.9—7.4 (m) |
| 10 | 3-Cl | — | CH$_3$ | CH$_3$ | H | S | 0.9-1.1 (m), 2.9 (mc), 3.2-3.8 (m), 4.9 (mc), 7.1-7.4 (m) |
| 11 | 3-Cl | — | C$_6$H$_5$ | CH$_3$ | H | S | 1.0 (mc), 2.95 (mc), 3.95 (mc), 4.4 (mc), 5.0 (mc), 7.15-7.45 (m) |
| 12 | 3-Cl | — | C$_6$H$_6$ | H | H | S | 2.95 (mc), 3.7 (mc), 4.0 (mc), 4.9-5.15 (m), 7.1-7.4 (m), 7.5 (br s) |

TABLE 1-continued (Ia)

| Ex. | $(R^1)_n$ | $(R^2)_m$ | $R^{5a}$ | $R^{5c}$ | $R^{5d}$ | X | Physico-chemical data (m.p. [° C.]; $^1$H-NMR (CDCl$_3$): δ [ppm]; HPLC-MS: RT [min], molecular mass |
|---|---|---|---|---|---|---|---|
| 13 | — | — | C$_6$H$_5$ | H | H | S | 2.95 (mc), 3.7 (mc), 4.05 (mc), 4.9-5.1 (m), 7.15-7.4 (m), 7.5 (brs) |
| 14 | 2-F | — | H | H | H | S | 3.1 (mc), 3.2 (t), 3.8 S (mc), 4.9 (t), 6.9-7.35 (m) |
| 15 | 4-Cl | — | H | H | H | S | 3.0-3.4 (m), 3.85 (mc), 4.75 (mc), 6.9-7.4 (m) |
| 16 | 3-CH$_3$ | — | CH$_3$ | H | H | S | 1.3 (d), 2.3 (s), 3.05 (d), 3.5 (mc), 3.9 (mc), 4.9 (mc), 6.8-7.4 (m) |
| 17 | 3-CH$_3$ | — | C$_6$H$_5$ | H | H | S | 2.3 (s), 3.1 (mc), 3.95 (mc), 4.25 (mc), 4.85-5.1 (m), 6.8-7.35 (m) |
| 18 | 3-CH$_3$ | — | H | H | H | S | 2.3 (s), 3.1 (mc), 3.3 (mc), 3.9 (mc), 4.8 (mc), 6.8-7.3 (m) |
| 19 | 3-F | — | H | H | H | S | 2.85-3.35 (m), 3.85 (mc), 4.75 (mc), 6.8-7.4 (m) |
| 20 | 3-Cl, 4-F | — | H | H | H | S | 2.90 (mc), 3.15 (t), 3.65 (t), 4.85 (mc), 7.2-7.5 (m) |
| 21 | 3-F, 4-F | — | H | H | H | S | 103-105° C. |
| 22 | 4-Br | — | H | H | H | S | 2.9 (mc), 3.1 (t), 3.65 (t), 4.9 (mc), 7.15-7.4 (m) |
| 23 | — | 3-OCH$_3$, 5-OCH$_3$ | H | H | H | O | — |
| 24 | 3-Cl | — | H | H | H | O | 112-113° C. |
| 25 | 4-CH$_3$ | — | H | H | H | O | — |
| 26 | 2-Br | — | H | H | H | O | — |
| 27 | 2-Cl, 4-Cl | — | H | H | H | O | — |
| 28 | — | 3-Cl, 4-Cl | H | H | H | O | — |
| 29 | — | — | H | CH$_3$ | CH$_3$ | O | 2.722 295 [M + H]+ |
| 30 | — | — | CH$_3$ | H | H | O | 2.706 281 [M + H]$^+$ |
| 31 | — | — | H | C$_2$H$_5$ | H | O | 2.779 295 [M + H]$^+$ |
| 32 | — | — | CH$_3$ | CH$_3$ | H | O | 2.826 295 [M + H]$^+$ |
| 33 | — | — | H | CH$_3$ | H | O | 2.660 281 [M + H]$^+$ |
| 34 | 2-F | — | H | H | H | O | 157-158° C. |
| 35 | 3-F, 5-F | — | H | H | H | O | 129-130° C. |
| 36 | 3-F | — | H | H | H | O | 117-118° C. |
| 37 | 3-Cl | — | H | CH$_3$ | CH$_3$ | O | 2.890 329 [M + H]$^+$ |
| 38 | 3-Cl | — | CH$_3$ | H | H | O | 2.912 315 [M + H]$^+$ |
| 39 | 3-Cl | — | H | C$_2$H$_5$ | H | O | 2.992 329 [M + H]$^+$ |

TABLE 1-continued (Ia)

| Ex. | $(R^1)_n$ | $(R^2)_m$ | $R^{5a}$ | $R^{5c}$ | $R^{5d}$ | X | Physico-chemical data (m.p. [° C.]; $^1$H-NMR (CDCl$_3$): δ [ppm]; HPLC-MS: RT [min], molecular mass |
|---|---|---|---|---|---|---|---|
| 40 | 3-Cl | — | CH$_3$ | CH$_3$ | H | O | 2.016 329 [M + H]$^+$ |
| 41 | 3-Cl, 4-Cl | — | H | H | H | O | 168-169° C. |
| 42 | 2-Cl | — | H | H | H | O | 141-143° C. |
| 43 | 3-Br | — | H | H | H | O | 110-111° C. |
| 44 | 2-Cl, 6-Cl | — | H | H | H | O | 187-188° C. |
| 50 | — | — | H | H | H | S | 114-116° C. |
| 51 | 4-CH$_3$ | — | H | H | H | S | 2.25 (s), 3.0 (mc), 3.5-3.9 (m), 5.1 (mc), 7.05-7.45 (m)* |
| 52 | 3-Br | — | H | H | H | S | 2.9 (mc), 3.1 (t), 3.65 (t), 4.9 (mc), 7.15-7.4 (m)* |
| 53 | 2-Cl | 4-F | H | H | H | S | 120-122° C. |
| 54 | 2-CH$_3$ | — | H | H | H | S | 2.2 (s), 3.1 (mc), 3.2 (t), 3.9 (t), 4.9 (t), 7.0-7.35 (m) |
| 55 | 4-OCH$_3$ | 4-OCH$_3$ | H | H | H | S | 3.0-3.2 (m), 3.25 (t), 3.75-3.85 (m), 4.5 (t), 6.65-7.2 (m) |
| 56 | 4-Br | — | H | H | H | S | 3.0-3.15 (m), 3.85 (t), 4.85 (t), 6.9-7.3 (m) |
| 57 | — | 4-CH$_3$ | H | H | H | S | 120-123° C. |
| 58 | — | 3-CH$_3$ | H | H | H | S | 98-100° C. |
| 59 | 3-CF$_3$ | — | H | H | H | S | 3.1 (mc), 3.25 (mc), 3.9 (t), 4.9 (t), 7.2-7.45 (m) |
| 60 | 2-Cl, 4-F | — | H | H | H | S | 3.0 (mc), 3.15 (t), 3.65 (t), 4.95 (mc), 7.15-7.4 (m)* |
| 61 | 3-Cl, 5-Cl | — | H | H | H | S | 110-111° C. |
| 62 | 2-F, 3-F, 4-F, 5-F, 6-F | — | H | H | H | S | 143-145° C. |
| 63 | 3-(m-F-Ph) | — | H | H | H | S | 376 [M + H]$^+$ |
| 64 | 3-(p-OCH$_3$-Ph) | — | H | H | H | S | 2.95 (mc), 3.1 (t), 3.7 (mc), 3.8 (s), 4.95 (mc), 7.0-7.45 (m)* |
| 65 | — | 2-Cl, 6-Cl | H | H | H | S | 134-136° C. |
| 66 | 3-CH$_3$ | 2-Cl, 3-Cl | H | H | H | S | 158-159° C. |
| 67 | 3-CH$_3$ | 2-Cl, 6-Cl | H | H | H | S | 148-150° C. |
| 68 | — | 4-C$_2$H$_5$ | H | H | H | S | 120-121° C. |
| 69 | — | 4-S-CH$_3$ | H | H | H | S | 60-62° C. |
| 70 | — | 2-Cl, 3-Cl | H | H | H | S | 151-152° C. |
| 71 | 3-Cl | 3-Cl | H | H | H | S | 351 [M + H]$^+$ |
| 72 | — | 3-O—CH$_3$ | H | H | H | S | 312 [M + H]$^+$ |
| 73 | — | 2-CH$_3$, 4-CH$_3$ | H | H | H | S | 2.2 (s), 2.3 (s), 3.05 (mc), 3.2 (t), 3.85 (t), 5.05 (t), 6.9-7.3 (m) |
| 74 | — | 4-O-t-Butyl | H | H | H | S | 1.3 (s), 3.0-3.15 (m), 3.25 (t), 3.9 (t), 4.9 (t), 6.9-7.2 (m) |
| 75 | — | 3-O—C$_2$H$_5$ | H | H | H | S | 1.4 (t), 3.05 (mc), 3.2 (mc), 3.9 (mc), 4.9 (t), 6.7-7.7 (m) |
| 76 | — | 2-O—C$_2$H$_5$ | H | H | H | S | 1.45 (t), 3.05-3.25 (m), 3.9 (t), 4.05 (t), 5.1 (t), 6.8-7.2 (m) |

TABLE 1-continued (Ia)

| Ex. | $(R^1)_n$ | $(R^2)_m$ | $R^{5a}$ | $R^{5c}$ | $R^{5d}$ | X | Physico-chemical data (m.p. [° C.]; $^1$H-NMR (CDCl$_3$): δ [ppm]; HPLC-MS: RT [min], molecular mass |
|---|---|---|---|---|---|---|---|
| 77 | — | 2-C$_2$H$_5$ | H | H | H | S | 1.1 (t), 2.55 (mc), 3.1 (t), 3.2 (t), 3.9 (t), 5.2 (t), 7.1-7.2 (m) |
| 78 | 2-Cl | — | H | H | H | S | 3.15 (mc), 3.8 (mc), 4.95 (t), 7.1-7.35 (m) |
| 79 | 3-CH$_3$ | 4-C$_2$H$_5$ | H | H | H | S | 1.1 (t), 2.2 (s), 2.55 (mc), 2.7-2.95 (m), 3.1 (t), 3.65 (t), 4.85 (mc), 7.0-7.15 (m)* |
| 80 | 3-CH$_3$ | 4-S—CH$_3$ | H | H | H | S | 112-114° C. |
| 81 | — | 2-Cl | H | H | H | S | 101-105° C. |
| 82 | — | 3-Cl | H | H | H | S | 95-97° C. |
| 83 | 3-CH$_3$ | 2-Cl | H | H | H | S | 104-107° C. |
| 84 | — | 2-O—CH$_3$ | H | H | H | S | 3.1 (mc), 3.2 (t), 3.85 (mc), 5.0 (t), 6.85-7.2 (m) |
| 85 | 3-CH$_3$ | 4-Cl | H | H | H | S | 143-146° C. |
| 86 | — | 2-F | H | H | H | S | 102-103° C. |
| 87 | — | 4-F | H | H | H | S | 122-123° C. |
| 88 | 3-CH$_3$ | 2-CH$_3$ | H | H | H | S | 128-130° C. |
| 89 | 3-CH$_3$ | 3-CH$_3$ | H | H | H | S | 2.25 (s), 2.35 (s), 3.0 (mc), 3.2 (mc), 3.9 (mc), 4.9 (t), 6.8-7.2 (m) |
| 90 | — | 3-F | H | H | H | S | 119-120° C. |
| 91 | — | 2-Br | H | H | H | S | 3.1 (mc), 3.3 (mc), 3.9 (t), 4.95 (mc), 7.2-7.7 (m) |
| 92 | — | 3-Br | H | H | H | S | 3.1 (mc), 3.35 (mc), 3.85 (mc), 4.35 (mc), 7.2-7.5 (m) |
| 93 | 3-CF$_3$ | — | H | H | H | O | 121-123° C. |
| 94 | — | 2-CH$_3$, 4-t-Butyl | H | H | H | S | 258-260° C. (HCl-salt) |
| 95 | — | 2-CH$_3$, 4-O—CH$_3$, 5-CH$_3$ | H | H | H |  | 124-126° C. |
| 96 | — | 2-Cl, 3-Cl, 4-O—CH$_3$ | H | H | H | S | 182-184° C. |
| 97 | — | 4-O—CH$_3$ | H | H | H | S | 2.8-3.0 (m), 3.15 (t), 3.65 (mc), 4.8 (mc), 7.1-7.2 (m)* |
| 98 | 3-CH$_3$ | 3-Cl | H | H | H | S | 2.2 (s), 2.8-2.95 (m), 3.65 (mc), 4.85 (mc), 7.15-7.4 (m)* |
| 99 | 3-CH$_3$ | 2-O—CH$_3$ | H | H | H | S | 2.25 (s), 2.65-2.85 (m), 3.1 (t), 3.65 (t), 3.8 (s), 5.2 (mc), 6.9-7.2 (m)* |
| 100 | 3-CH$_3$ | 4-O—CH$_3$ | H | H | H | S | 2.25 (s), 2.75-2.95 (m), 3.1 (t), 3.65 (t), 4.8 (mc), 5.75 (s), 6.8-7.2 (m)* |
| 101 | 3-CH$_3$ | 3-O—CH$_3$ | H | H | H | S | 2.25 (s), 2.8-2.95 (m), 3.1 (t), 3.7 (mc), 4.85 (mc), 6.75-7.2 (m)* |
| 102 | 3-CH$_3$ | 2-Cl, 3-Cl | H | H | H | O | 203-206° C. |

TABLE 1-continued (Ia)

| Ex. | $(R^1)_n$ | $(R^2)_m$ | $R^{5a}$ | $R^{5c}$ | $R^{5d}$ | X | Physico-chemical data (m.p. [° C.]; $^1$H-NMR (CDCl$_3$): δ [ppm]; HPLC-MS: RT [min], molecular mass |
|---|---|---|---|---|---|---|---|
| 103 | 3-O—CH$_3$, 5-O—CH$_3$ | — | H | H | H | S | 2.675 343 [M + H]$^+$ |
| 104 | — | 4-Br | H | H | H | S | 3.1 (mc), 3.35 (mc), 3.9 (mc), 4.35 (mc), 7.2-7.5 (m) |
| 105 | - | 3-O—CH$_2$—C$_6$H$_5$ | H | H | H | S | 2.95 (mc), 3.2 (t), 3.8 (mc), 4.8 (t), 5.2 (mc), 6.5-7.4 (m) |
| 106 | 3-CH$_3$ | 2-F | H | H | H | S | 2.2 (s), 2.8-2.95 (m), 3.15 (t), 5.2 (mc), 6.95-7.4 (m)* |
| 107 | 3-CH$_3$ | 3-F | H | H | H | S | 205-207° C. |
| 108 | — | 2-(O-2-Butenyl) | H | H | H | S | 1.7 (mc), 2.7 (mc), 2.9 (mc), 3.1 (t), 3.6 (t), 4.45-4.55 (m), 5.2 (mc), 5.7-5.9 (m), 6.9 (mc), 7.1-7.3 (m)* |
| 109 | — | 2-O-CH$_3$, 3-O-CH$_3$ | H | H | H | S | 109-113° C. |
| 110 | — | 2-(S-[p-Cl-C$_6$H$_4$]) | H | H | H | S | 2.8-2.9 (m), 3.1 (t), 3.6 (mc), 5.45 (mc), 7.15-7.6 (m)* |
| 111 | — | 2-O-CH$_2$-C$_6$H$_5$, 3-O-CH$_3$ | H | H | H | S | 126-131° C. |
| 112 | — | 2-CH$_3$, 3-C$_6$H$_5$ | H | H | H | S | 172-174° C. |
| 113 | — | 2-CF$_3$, 3-C$_6$H$_5$ | H | H | H | S | 167-169° C. |
| 114 | — | 2-F, 3-F | H | H | H | S | 103-106° C. |
| 115 | — | 2-CH$_3$, 3-F | H | H | H | S | 137-139° C. |
| 116 | — | 2-F, 3-CF$_3$ | H | H | H | S | 95-98° C. |
| 117 | 3-CH$_3$ | 4-F | H | H | H | S | 2.3 (s), 3.0 (mc), 3.25 (t), 3.9 (t), 4.9 (mc), 6.8-7.2 (m) |
| 118 | 3-CH$_3$ | 4-CH$_3$ | H | H | H | S | 107-109° C. |
| 119 | 3-CH$_3$ | 2-O—CH$_3$, 3-O—CH$_3$ | H | H | H | S | 126-129° C. |
| 120 | 3-CH$_3$ | 2-(O-2-Butenyl) | H | H | H | S | 88-93° C. |
| 121 | — | 2-CH$_3$, 3-CH$_3$ | H | H | H | S | 116-120° C. |
| 122 | 3-CH$_3$ | 2-F, 3-F | H | H | H | S | 94-97° C. |
| 123 | 3-CH$_3$ | 2-CH$_3$, 3-CH$_3$ | H | H | H | S | 124-127° C. |
| 124 | — | 2-Cl, 3-CF$_3$ | H | H | H | S | 121-123° C. |
| 125 | 3-CH$_3$ | — | H | H | H | O | 123-124° C. |
| 126 | — | 2-CH$_3$, 3-CF$_3$ | H | H | H | S | 133-136° C. |
| 127 | 3-CH$_3$ | 3-(O-[p-t-Butyl-C$_6$H$_4$]) | H | H | H | S | 1.35 (s), 2.3(s), 3.0 (t), 3.2 (t), 3.9(t), 4.9 (mc), 6.8-7.35 (m) |
| 128 | 3-CH$_3$ | 3-O—CF$_3$ | H | H | H | S | 2.2 (s), 2.8-2.95 (mc), 3.15 (t), 3.65 (t), 4.9 (mc), 6.95-7.4 (m)* |
| 129 | — | 2-—(CH$_2$-Naphthyl) | H | H | H | S | 2.6 (mc), 2.8 (mc), 3.1 (t), 3.6 (t), 5.25 (mc), 5.6 (mc), 6.75-7.55 (m)* |
| 130 | - | 2-F, 3-Cl | H | H | H | S | 2.8-3.0 (m), 3.1 (mc), 3.7 (mc), 5.2 (mc), 7.2-7.4 (m)* |
| 131 | 3-CH$_3$ | 2-CH$_3$, 3-F | H | H | H | S | 134-136° C. |
| 132 | 3-CH$_3$ | 2-F, 3-F$_3$ | H | H | H | S | 127-130° C. |

TABLE 1-continued (Ia)

A structure is shown with two phenyl rings bearing $(R^1)_n$ and $(R^2)_m$ substituents, connected through a CH-NH group to a 5-membered ring containing X, N, and substituents $R^{5a}$, $R^{5c}$, $R^{5d}$.

| Ex. | $(R^1)_n$ | $(R^2)_m$ | $R^{5a}$ | $R^{5c}$ | $R^{5d}$ | X | Physico-chemical data (m.p. [° C.]; $^1$H-NMR (CDCl$_3$): δ [ppm]; HPLC-MS: RT [min], molecular mass |
|---|---|---|---|---|---|---|---|
| 133 | 3-CH$_3$ | 2-Cl, 3-CF$_3$ | H | H | H | S | 139-142° C. |
| 134 | 3-CH$_3$ | 2-F, 3-Cl | H | H | H | S | 111-114° C. |
| 135 | 3-CH$_3$ | 2-CH$_3$, 3-CF$_3$ | H | H | H | S | 129-131° C. |
| 136 | 4-CH$_3$ | 2-Cl, 3-Cl | H | H | H | O | 224-225° C. |
| 137 | 3-CH$_3$ | 2-F, 4-Cl | H | H | H | O | 117-118° C. |
| 138 | 3-CH$_3$ | 2-Cl, 4-F | H | H | H | O | 178-179° C. |
| 139 | 4-Benzyl | — | H | H | H | S | 155-156° C. |
| 140 | 4-Benzyl | 2-Cl, 3-Cl | H | H | H | S | 175-177° C. |
| 141 | 3-CH$_3$ | 2-F, 4-F, 5-F | H | H | H | S | 2.3 (s), 3.05 (mc), 3.25 (t), 3.8 (mc), 5.05 (mc), 6.85-7.15 (m) |
| 142 | 2-CH$_3$, 4-CH$_3$ | 2-Cl, 3-Cl | H | H | H | S | 2.2 (2 x s), 2.6-2.8 (mc), 3.15 (t), 3.6 (mc), 5.2 (mc), 6.9-7.55 (m)* |
| 143 | 3-CH$_3$, 4-CH$_3$ | — | H | H | H | S | 2.2 (2 x s), 3.0 (mc), 3.2 (mc), 3.85 (mc), 4.9 (mc), 6.75-7.35 (m) |
| 144 | 3-CH$_3$ | 3-Br, 5-Br | H | H | H | O | 128-130° C. |
| 145 | 3-CH$_3$ | 2-Cl, 5-Cl | H | H | H | O | 189-191° C. |
| 146 | 3-CH$_3$ | 2-Cl, 5-Cl | H | H | H | S | 125-127° C. |
| 147 | 3-CH$_3$ | 3-Br, 5-Br | H | H | H | S | 127-130° C. |
| 148 | 3-CH$_3$ | 2-Cl, 3-Cl, 4-CH$_3$ | H | H | H | S | 205-208° C. |
| 149 | 3-CH$_3$ | 2-F, 3-F, 6-F | H | H | H | S | 2.25 (s), 3.05 (mc), 3.25 (t), 3.9 (t), 5.45 (mc), 6.85-7.1 (m) |
| 150 | 3-CH$_3$ | 2-F, 3-F, 5-F | H | H | H | S | 2.3 (s), 3.0 (mc), 3.25 (t), 3.85 (mc), 5.15 (mc) 6.7-7.15 (m) |
| 151 | 3-CH$_3$ | 2-F, 6-F, 3-Cl | H | H | H | S | 3.315 367 [M+ H]$^+$ |
| 152 | 3-CH$_3$ | 2-Br | H | H | H | S | 2.35 (s), 3.05 (mc), 3.25 (mc), 3.8 (mc), 4.9 (mc), 7.05-7.65 (m) |
| 153 | 3-CH$_3$ | 3-Br | H | H | H | S | 2.913 377 [M + H]$^+$ |
| 154 | 3-CH$_3$ | 4-Br | H | H | H | S | 135-136° C. |
| 155 | 3-CH$_3$ | 2-F, 6-Cl | H | H | H | S | 96-97° C. |
| 156 | 3-CH$_3$ | 2-Cl, 4-Cl | H | H | H | S | 2.35 (s), 3.0 (mc), 3.25 (mc), 3.85 (mc), 5.0 (mc), 7.05-7.5 (m) |
| 157 | 3-CH$_3$ | 3-Cl, 4-Cl | H | H | H | S | 2.3 (s), 3.0 (mc), 3.25 (t), 3.85 (mc), 4.85 (t), 6.8-7.35 (m) |
| 158 | 3-CH$_3$ | 3-F, 5-F | H | H | H | S | 2.25 (s), 3.0 (mc), 3.2 (mc), 3.85 (mc), 4.85 (mc), 6.65-7.15 (m) |
| 159 | 3-CH$_3$ | 2-Cl, 3-Cl | H | H | H | O | 165-167° C. |
| 160 | 3-CH$_3$ | 3-Cl, 4-Cl | H | H | H | O | 127-130° C. |
| 161 | 3-CH$_3$ | 2-F, 6-Cl | H | H | H | O | 109-111° C. |
| 162 | 3-CH$_3$ | 3-F, 5-F | H | H | H | O | 146-148° C. |
| 163 | 4-CH$_3$ | 2-Cl, 3-Cl | H | H | H | S | 168-169° C. |

TABLE 1-continued (Ia)

|  |  |  |  |  |  | Physico-chemical data (m.p. [° C.]; ¹H-NMR (CDCl₃): δ [ppm]; HPLC-MS: RT [min], |
|---|---|---|---|---|---|---|
| Ex. | $(R^1)_n$ | $(R^2)_m$ | $R^{5a}$ | $R^{5c}$ | $R^{5d}$ | X | molecular mass |
| 164 | 3-CH₃ | 2-F, 5-Br | H | H | H | S | 3.119<br>393 [M + H]⁺ |
| 165 | — | 3,4-(Methylen-dioxy)phenyl | H | H | H | S | 120-122° C. |
| 166 | 3-(—O—CH₂—O—),<br>4-(—O—CH₂—O—) | — | H | H | H | S | 2,638<br>326 [M + H]⁺ |
| 167 | — | 3-Methoxy-naphth-2-yl | H | H | H | S | 362 [M + H]⁺ |

EXAMPLE 45

[2-(3-Chlorophenyl)-1-phenylethylimino]-thiazolidine-3-carboxylic acid methyl ester A mixture of 1-[2-(3-Chlorophenyl)-2-phenyl-ethyl]-(4,5-dihydrothiazol-2-yl)-amine (0.50 g), potassium carbonate (0.33 g), Dimethylformamid (10 ml) and 2-3 drops of triethyl amine was treated with methyl chloro formate (0.18 g) at room temperature and stirred overnight. Dilution with water and extraction into tert.-butyl methyl ether gave a crude product which was purified by column chromatography on silica to yield [2-(3-Chlorophenyl)-1-phenylethylimino]-thiazolidine-3-carboxylic acid methyl ester (0.25 g).

EXAMPLE 46

[2-(3-Chlorophenyl)-1-phenylethylimino]-thiazolidine-3-carbonitrile

A mixture of 1-[1-(4-Chlorophenyl)-2-phenyl-ethyl]-(4,5-dihydrothiazol-2-yl)-amine (0.50 g), potassium carbonate (0.33 g), Dimethylformamid (10 ml) and 2-3 drops of triethyl amine was treated with bromocyan at room temperature and stirred overnight, followed by stirring for 3 h at 50° C. Water was added and the reaction mixture was extracted with methyl-tert.-butylether. After drying the solvent was evaporated and the residue was subjected to chromatography on silica gel to yield 19% of the nitrile.

The compounds of the general formula Ib (examples 47 to 49) were prepared accordingly. The spectroscopical data of these compounds are listed in table 2.

TABLE 2

(Ib)

| Ex. | $(R^1)_m$ | $(R^2)_n$ | $R^6$ | X | Physico-chemical data (m.p. [° C.]; ¹H-NMR (CDCl₃): δ [ppm]; HPLC-MS: RT [min], molecular mass |
|---|---|---|---|---|---|
| 45 | 3-Cl | — | C(O)OCH₃ | S | 2.95-3.2 (m), 3.9 (s), 4.0 (mc), 4.25 (mc), 6.95-7.35 (m) |
| 46 | 3-Cl | — | CN | S | 3.05 (mc), 3.20 (mc), 3.80 (mc), 4.15 (mc), 7.0-7.4 (m) |

TABLE 2-continued (Ib)

[Structure: Diphenylmethyl group with (R¹)ₙ on one phenyl and (R²)ₘ on the other, central CH bonded to H and N=C(X)-CH₂-CH₂-N(R⁶) forming a 5-membered ring]

| Ex. | (R¹)ₘ | (R²)ₙ | R⁶ | X | Physico-chemical data (m.p. [° C.]; ¹H-NMR (CDCl₃): δ [ppm]; HPLC-MS: RT [min], molecular mass |
|---|---|---|---|---|---|
| 47 | — | — | $C_2H_5$ | S | 1.0 (mc), 2.9-3.5 (m), 4.1 (mc), 7.0-7.3 (m) |
| 48 | 3-Cl | — | $C_2H_5$ | S | 1.15 (t), 3.0 (mc), 3.3-3.6 (m), 4.15 (mc), 6.9-7.4 (m) |
| 49 | 3-F | — | $CH_3$ | O | 2.80 (s), 2.95 (d), 3.2 (mc), 3.9-4.1 (m), 4.75 (mc), 6.75-7.35 (m) |
| 168 | 3-Cl | — | $COOCH_3$ | O | 358 [M + H]⁺ |

Cotton Aphid (*Aphis gossypii*)

Cotton plants in the cotyledon stage (variety 'Delta Pine') are infested with approximately 100 laboratory-reared aphids by placing infested leaf sections on top of the test plants. The leaf sections are removed after 24 hr. The cotyledons of the intact plants are dipped into gradient solutions of the test compound. Aphid mortality on the treated plants, relative to mortality on check plants, is determined after 5 days.

In this test, compounds of examples nos 14, 18, 19, 24, 25, 26, 29, 35, 36, 41, 42, 43 and 45, 51, 52, 53, 61, 64, 70, 79, 82, 83, 100, 101, 114, 118, 123, 124, 131, 132, 133, 134, 135, 142, 144, 147, 150, 155, 159, 162 and 163 at 300 ppm showed over 80% mortality in comparison with untreated controls.

Green Peach Aphid (*Myzus persicae*)

Pepper plants in the 2ⁿᵈ leaf-pair stage (variety 'California Wonder') are infested with approximately 40 laboratory-reared aphids by placing infested leaf sections on top of the test plants. The leaf sections are removed after 24 hr. The leaves of the intact plants are dipped into gradient solutions of the test compound. Aphid mortality on the treated plants, relative to mortality on check plants, is determined after 5 days.

In this test, compounds of examples nos. 5, 6, 7, 14, 15, 16, 18, 19, 23, 24, 25, 26, 27, 29, 30, 33, 34, 35, 36, 38, 41, 42, 43, 44, 45, 46 and 49, 51, 52, 54, 56, 63, 70, 71, 76, 78, 81, 83, 91, 98, 99, 101, 102, 103, 108, 115, 119, 122, 125, 130, 132, 136, 137, 141, 144, 156, 157, 160, 161 and 164 at 300 ppm showed over 80% mortality in comparison with untreated controls.

Bean Aphid (*Aphis fabae*)

Nasturtium plants in the 1ˢᵗ leaf-pair stage (variety 'Mixed Jewel') are infested with approximately 25 laboratory-reared aphids by placing infested cut plants on top of the test plants. The cut plants are removed after 24 hr. The foliage and stem of the test plants are dipped into gradient solutions of the test compound. Aphid mortality is determined after 3 days.

In this test, compounds of examples no. 6, 66, 93, 146 and 162 at 300 ppm showed over 80% mortality in comparison with untreated controls.

2. Examples of Action Against Pests

The action of the compounds of the formula I against pests was demonstrated by the following experiments:

The active compounds were formulated a. for testing the activity against *Aphis gossypii, Myzus persicae*, and *Aphis fabae*, as 50:50 acetone:water solutions amended with 100 ppm Kinetic® (surfactant), b. for testing the activity against *Spodoptera eridania* as a 10.000 ppm solution in a mixture of 35% acetone and water, which was diluted with water, if needed, After the experiments were completed, in each case the lowest concentration was determined at which the compound still caused an 75 to 100% inhibition or mortality in comparison with untreated controls (limit or minimal concentration).

Cotton Aphid (*Aphis gossypii*)

Cotton plants in the cotyledon stage (variety 'Delta Pine') are infested with approximately 100 laboratory-reared aphids by placing infested leaf sections on top of the test plants. The leaf sections are removed after 24 hr. The cotyledons of the intact plants are dipped into gradient solutions of the test compound. Aphid mortality on the treated plants, relative to mortality on check plants, is determined after 5 days.

In this test, compounds of examples nos 14, 18, 19, 24, 25, 26, 29, 35, 36, 41, 42, 43 and 45 at 300 ppm showed over 80% mortality in comparison with untreated controls.

Green Peach Aphid (*Myzus persicae*)

Pepper plants in the 2ⁿᵈ leaf-pair stage (variety 'California Wonder') are infested with approximately 40 laboratory-reared aphids by placing infested leaf sections on top of the test plants. The leaf sections are removed after 24 hr. The leaves of the intact plants are dipped into gradient solutions of the test compound. Aphid mortality on the treated plants, relative to mortality on check plants, is determined after 5 days.

In this test, compounds of examples nos. 5, 6, 7, 14, 15, 16, 18, 19, 23, 24, 25, 26, 27, 29, 30, 33, 34, 35, 36, 38, 41, 42, 43, 44, 45, 46 and 49 at 300 ppm showed over 80% mortality in comparison with untreated controls.

Bean Aphid (*Aphis fabae*)

Nasturtium plants in the 1ˢᵗ leaf-pair stage (variety 'Mixed Jewel') are infested with approximately 25 laboratory-reared aphids by placing infested cut plants on top of the test plants. The cut plants are removed after 24 hr. The foliage and stem of the test plants are dipped into gradient solutions of the test compound. Aphid mortality is determined after 3 days.

In this test, compounds of examples no. 6 at 300 ppm showed over 80% mortality in comparison with untreated controls.

Southern armyworm (*Spodoptera eridania*), 2nd Instar Larvae

Foliage of two Sieva lima beans plants at the first expanded true-leaf stage that are contained within a single 3.8 cm square plastic pot are dipped into the test solution with agitation for 3 seconds and allowed to dry in a hood. The pot is then placed in a 25.4 cm plastic zipper top bag and infested with ten $2^{nd}$ instar caterpillars. At 5 days, observations are made of mortality, reduced feeding, or any interference with normal molting.

In this test, compounds of examples nos. 16 at 300 ppm showed over 50% mortality in comparison with untreated controls.

The invention claimed is:
1. 1-(Azolin-2-yl)amino-1,2-diphenylethane compounds of the general formula (I):

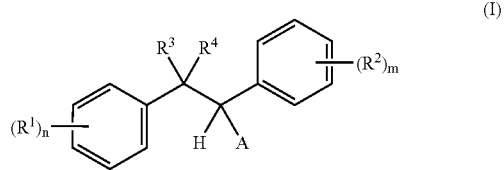

wherein A is a radical of the formulae $A^1$ or $A^2$:

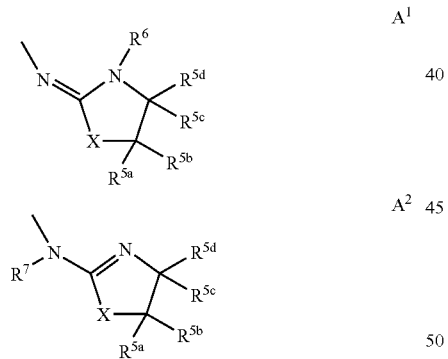

and wherein
m is 0, 1, 2, 3, 4 or 5;
n is 0, 1, 2, 3, 4 or 5;
X is sulfur or oxygen;
$R^1$, $R^2$ are each independently halogen, OH, SH, $NH_2$, $SO_3H$, COOH, cyano, nitro, $C_1$-$C_6$-alkyl, $C_1$-$C_6$-alkoxy, $C_1$-$C_6$-alkylamino, di($C_1$-$C_6$-alkyl)amino, $C_1$-$C_8$-alkylthio, $C_2$-$C_6$-alkenyl, $C_2$-$C_6$-alkenyloxy, $C_2$-$C_6$-alkenylamino, $C_2$-$C_6$-alkenylthio, $C_2$-$C_6$-alkynyl, $C_2$-$C_6$-alkynyloxy, $C_2$-$C_6$-alkynylamino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkynylsulfonyl, formyl, $C_1$-$C_6$-alkylcarbonyl, $C_2$-$C_6$-alkenylcarbonyl, $C_2$-$C_6$-alkynylcarbonyl, $C_1$-$C_6$-alkoxycarbonyl, $C_2$-$C_6$-alkenyloxycarbonyl, $C_2$-$C_6$-alkynyloxy carbonyl, carbonyloxy, $C_1$-$C_6$-alkylcarbonyloxy, $C_1$-$C_6$-alkenyl carbonyl oxy, $C_1$-$C_6$-alkynyl carbonyloxy, wherein the carbon atoms in the aliphatic radicals of the aforementioned groups may carry any combination of 1, 2 or 3 radicals $R^\#$, $C(O)NR^aR^b$, $(SO_2)NR^aR^b$, wherein $R^a$ and $R^b$ are each independently hydrogen, $C_1$-$C_6$-alkyl, $C_2$-$C_6$-alkenyl, or $C_2$-$C_6$-alkynyl, wherein the carbon atoms in these groups may carry any combination of 1, 2 or 3 radicals $R^\#$, a radical Y—Ar or a radical Y—Cy, wherein
Y is a single bond, oxygen, sulfur, $C_1$-$C_6$-alkandiyl or alkandiyloxy,
Ar is phenyl, naphthyl or a mono- or bicyclic 5- to 10-membered heteroaromatic ring, which contains 1, 2, 3 or 4 heteroatoms selected from oxygen, sulfur and nitrogen as ring members, wherein Ar is unsubstituted or may carry any combination of 1, 2, 3, 4 or 5 radicals $R^\#$; and
Cy is $C_3$-$C_{12}$-cycloalkyl, which is unsubstituted or substituted with any combination of 1, 2, 3, 4 or 5 radicals $R^\#$.

and wherein two radicals $R^1$ or two radicals $R^2$ that are bound to adjacent carbon atoms of the phenyl rings may form together with said carbon atoms a fused benzene ring, a fused saturated or partially unsaturated 5-, 6-, or 7-membered carbocycle or a fused 5-, 6-, or 7-membered heterocycle, which contains 1, 2, 3 or 4 heteroatoms selected from oxygen, sulfur and nitrogen as ring members, and wherein the fused ring is unsubstituted or may carry any combination of 1, 2, 3, or 4 radicals $R^\#$;

$R^3$, $R^4$ are each independently hydrogen, $C_1$-$C_6$-alkyl, $C_1$-$C_6$-haloalkyl, $C_3$-$C_6$-cycloalkyl, wherein the carbon atoms in these groups may carry any combination of 1, 2 or 3 radicals $R^\#$, phenyl or benzyl, each unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups;

$R^{5a}$, $R^{5b}$, $R^{5c}$, $R^{5d}$ are each in dependently hydrogen, $C_1$-$C_6$-alkyl, $C_1$-$C_6$-haloalkyl, $C_1$-$C_6$-alkylamino, $C_1$-$C_6$-alkoxy, $C_3$-$C_6$-cycloalkyl, wherein the carbon atoms in these groups may carry any combination of 1, 2 or 3 radicals $R^\#$, halogen, cyano, nitro, hydroxy, mercapto, amino, phenyl or benzyl, each unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups;

$R^6$ is hydrogen, cyano, nitro, $C_1$-$C_6$-alkyl, formyl, $C_1$-$C_6$-alkylcarbonyl, $C_1$-$C_6$-alkoxycarbonyl, $C_1$-$C_6$-alkylthiocarbonyl, wherein the carbon atoms in the aliphatic radicals of the aforementioned groups may carry any combination of 1, 2 or 3 radicals $R^\#$, $C(O)NR^aR^b$, or $(SO_2)NR^aR^b$, wherein $R^a$ and $R^b$ are as defined above, phenyl, phenyloxy, or benzyl, each of the last three mentioned radicals may be unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups;

$R^7$ is hydrogen, cyano, nitro, $C_1$-$C_6$-alkyl, formyl, $C_1$-$C_6$-alkylcarbonyl, $C_1$-$C_6$-alkoxycarbonyl, wherein the carbon atoms in the aliphatic radicals of the aforementioned groups may carry any combination of 1, 2 or 3 radicals $R^\#$, $C(O)NR^aR^b$, or $(SO_2)NR^aR^b$, wherein $R^a$ and $R^b$ are as defined above, phenyl, phenyloxy or benzyl, each of the last three mentioned groups may be unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups; and $R^\#$ is halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy, or $C_1$-$C_6$-alkylthio;

and the agriculturally acceptable salts thereof.

2. The compounds as claimed in claim 1, wherein $R^3$ is hydrogen or $C_1$-$C_4$-alkyl.

3. The compounds as claimed in claim 1, wherein $R^4$ is hydrogen, $C_1$-$C_4$-alkyl, $C_1$-$C_4$-haloalkyl, $C_1$-$C_4$-alkoxy-$C_1$-$C_4$-alkyl, or phenyl, which is unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups.

4. The compounds as claimed in claim 2, wherein $R^4$ is hydrogen, $C_1$-$C_4$-alkyl, $C_1$-$C_4$-haloalkyl, $C_1$-$C_4$-alkoxy-$C_1$-$C_4$-alkyl, or phenyl, which is unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups.

5. The compounds as claimed claim 1, wherein both $R^3$ and $R^4$ are hydrogen.

6. The compounds as claimed in claim 1, wherein $R^3$ is hydrogen and $R^4$ is selected from $C_1$-$C_4$-alkyl, $C_1$-$C_4$-haloalkyl, $C_1$-$C_4$-alkoxy-$C_1$-$C_4$-alkyl, or phenyl, which is unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups.

7. The compounds as claimed in claim 1, wherein A in formula I is a radical $A^1$, wherein $R^6$ is hydrogen, $C_1$-$C_4$-alkyl, formyl, $C_1$-$C_6$-alkylcarbonyl, $C_1$-$C_4$-haloalkylcarbonyl, $C_1$-$C_6$-alkoxycarbonyl, $C_1$-$C_4$-alkoxy-$C_1$-$C_4$-alkoxycarbonyl or alkylthiocarbonyl.

8. The compounds as claimed in claim 1, wherein A in formula I is a radical $A^2$, wherein $R^7$ is hydrogen.

9. The compounds as claimed in claim 1, wherein the radicals $R^{5a}$, $R^{5b}$, $R^{5c}$ and $R^{5d}$ are each hydrogen.

10. The compounds as claimed in claim 1, wherein at least one of the radicals $R^{5a}$, $R^{5b}$, $R^{5c}$ and $R^{5d}$ is different from hydrogen.

11. The compounds as claimed in claim 1, wherein n in formula I is 0, 1 or 2.

12. The compounds as claimed in claim 11, wherein n+m is an integer from 1, 2, 3 or 4.

13. The compounds as claimed in claim 1, wherein m in formula I is 0, 1 or 2.

14. The compounds as claimed in claim 13, wherein n+m is an integer from 1,2, 3 or 4.

15. The compounds as claimed in claimed in claim 1, wherein $R^1$ and $R^2$ are each independently selected from halogen, $C_1$-$C_4$-alkyl, $C_1$-$C_4$-alkoxy, $C_1$-$C_4$-haloalkyl, and phenyl, which is unsubstituted or substituted with any combination of 1 to 5 halogen, 1 to 3 $C_1$-$C_6$-alkyl, $C_1$-$C_6$-haloalkyl, $C_1$-$C_6$-alkylthio, $C_1$-$C_6$-haloalkylthio, $C_1$-$C_6$-alkoxy or $C_1$-$C_6$-haloalkoxy groups.

16. A method of combating animal pests selected from insects, arachnids and nematodes which comprises contacting said animal pests, their habit, breeding ground, food supply, plant, seed, soil, area, material or environment in which the animal pests are growing or may grow, or the materials, plants, seeds, soils, surfaces or spaces to be protected from attack or infestation by insects, arachnids or nematodes with a pesticidally effective amount of at least one 1-(azolin-2-yl)amino-1,2-diphenylethane compound of the general formula I as defined in claim 1 and/or at least one salt thereof.

17. A method for protecting crops from attack or infestation by insects, arachnids or nematodes which comprises contacting a crop with a pesticidally effective amount of at least one 1-(azolin-2-yl)amino-1,2-diphenylethane compound of the general formula I as defined in claim 1 and/or at least one salt thereof.

18. An agricultural composition comprising at least one 1-(azolin-2-yl)amino-1,2-diphenylethane compound of the general formula I as defined in claim 1 and/or at least one salt thereof and a solid or liquid carrier.

* * * * *

UNITED STATES PATENT AND TRADEMARK OFFICE
CERTIFICATE OF CORRECTION

PATENT NO. : 7,655,600 B2
APPLICATION NO. : 10/583710
DATED : February 2, 2010
INVENTOR(S) : Kordes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 692 days.

Signed and Sealed this

Twenty-third Day of November, 2010

David J. Kappos
*Director of the United States Patent and Trademark Office*